(12) United States Patent
Grimm et al.

(10) Patent No.: US 12,422,803 B2
(45) Date of Patent: Sep. 23, 2025

(54) OPTIMIZED PROCESS CONTROL

(71) Applicant: Sartorius Stedim Data Analytics AB, Umea (SE)

(72) Inventors: Christian Grimm, Heilbad Heiligenstadt (DE); Marek Höhse, Göttingen (DE); Johan Hultman, Malmö (SE); Chloe Lang, Copenhagen (DK)

(73) Assignee: Sartorius Stedim Data Analytics AB (SE)

( * ) Notice: Subject to any disclaimer, the term of this patent is extended or adjusted under 35 U.S.C. 154(b) by 1064 days.

(21) Appl. No.: 17/433,586

(22) PCT Filed: Feb. 25, 2020

(86) PCT No.: PCT/EP2020/054900
§ 371 (c)(1),
(2) Date: Aug. 24, 2021

(87) PCT Pub. No.: WO2020/173936
PCT Pub. Date: Sep. 3, 2020

(65) Prior Publication Data
US 2022/0137579 A1    May 5, 2022

(30) Foreign Application Priority Data
Feb. 26, 2019   (EP) .................................. 19159406

(51) Int. Cl.
*G05B 19/042*   (2006.01)
*G01N 21/65*   (2006.01)

(52) U.S. Cl.
CPC ........... *G05B 19/042* (2013.01); *G01N 21/65* (2013.01); *G05B 2219/32191* (2013.01)

(58) Field of Classification Search
CPC ...... G01N 1/02; G01N 21/65; G01N 35/0099; G05B 19/042; G05B 2219/32191; G16C 20/10
See application file for complete search history.

(56) References Cited

U.S. PATENT DOCUMENTS 9,541,471 B2    1/2017  McCready
2017/0177835 A1  6/2017  Cardoso-Menezes et al.
2017/0277829 A1  9/2017  Weggler et al.

FOREIGN PATENT DOCUMENTS

EP    3 291 038 A1    3/2018

OTHER PUBLICATIONS

International Search Report and Written Opinion, mailed Mar. 18, 2020, issued for International Patent Application No. PCT/EP2020/054900, 14 pages.

*Primary Examiner* — An H Do
(74) *Attorney, Agent, or Firm* — Klarquist Sparkman, LLP

(57) ABSTRACT

Aspects of the application relate to computer-implemented methods, process control devices, and a computer program. According to one aspect, a computer-implemented method for controlling a process in a plurality of first scale vessels via a first process control device is provided. Each of the first scale vessels contains fluid and the process is for producing a chemical, pharmaceutical, biopharmaceutical and/or biological product. The method includes controlling, by the first process control device and at least partially in parallel, the process in each of the first scale vessels. The method can include periodically determining, prior to an assigning decision and at a first frequency, first sets of process parameter values for each of the process parameters from each of the first scale vessels.

20 Claims, 10 Drawing Sheets

OPTIMIZED PROCESS CONTROL

CROSS REFERENCE TO RELATED APPLICATIONS

This is the U.S. National Stage of International Application No. PCT/EP2020/054900, filed Feb. 25, 2020, which was published in English under PCT Article 21(2), which in turn claims the benefit of European Patent Application No. 19 159 406.8, filed Feb. 26, 2019. The prior applications are incorporated herein by reference in their entirety.

The following description relates to a process for the production of a chemical, pharmaceutical, biopharmaceutical and/or biological product. In particular, aspects of the application relate to determining a multivariate process chart to be used to control a process to produce the product. Further aspects relate to controlling a process control device for determining the multivariate process chart and a method for controlling the process using the multivariate process chart. In addition, aspects of the application relate to a method for controlling vessels via a process control device in order to produce the product or to determine the multivariate process chart.

The process may be an industrial process and/or a bioprocess, such as a biotechnological process. The process may involve chemical or microbiological conversion of material in conjunction with the transfer of heat, mass, and energy. The process may include heterogeneous chemical reactions. The process may be a batch process, e.g., a fed-batch bioprocess. The process may involve producing cells for use in, or to host, the product. More particularly, the cells may host the product, or the cells may be (part of) the product.

Examples of inputs or ingredients (i.e., starting material) for the process may include biological material, such as bacteria, yeasts, fungi, molds, animal cells (e.g. mammalian, especially human, cells or insect cells), plant cells. Further ingredients may include one or more of the following: chemical compounds, protein such as enzymes, various biological substrates. Possible products may include recombinant and non-recombinant proteins, e.g. monoclonal antibodies (mAbs), vaccines, gene vectors, DNA, RNA, antibiotics, secondary metabolites, cells for cell therapy or regenerative medicine, half-synthesized products (e.g., artificial organs).

The multivariate process chart facilitates (i.e., may be used as a tool for) control of the process. The multivariate process chart may be implemented as a control chart, i.e., a process behavior chart. The multivariate process chart may include a process trajectory showing a desired path of development of the process over time, as well as upper and lower limits (i.e., warning or control limits) defined with respect to the trajectory. Values of process parameters from an actual or current process may be determined (e.g., measurements may be taken) and compared with the multivariate process chart in order to ensure that the process will result in production of a usable product, i.e., a product meeting at least one specified (e.g., predetermined) condition. The specified condition may relate to at least one process output or process parameter.

An advantage to using the multivariate process chart to control the process is that an actual trajectory (i.e., a process trajectory for the process being controlled) derived from process parameter values of the process can be compared with the multivariate process chart in order to recognize deviations of the actual trajectory from the trajectory of the multivariate process chart and to correct the deviations as early as possible. The early correction of process deviations, particularly those outside the upper or lower limits of the multivariate process chart, may result in the production of a product meeting the specified condition.

In the context of cells, process outputs may include a total quantity of cells, quantity of cells per unit volume of input fluid, a chemical composition of the cells, amount of cell debris, amount of shear damage or chemical damage, cell viability.

The multivariate process chart may be based on a batch evolution model. Each value in the trajectory may be derived at a different process maturity (e.g., at a different time during the process). The trajectory of the multivariate process chart may be referred to as a golden batch trajectory (i.e., a trajectory derived from the mean of multiple batch trajectories). The multivariate process chart may include upper and lower limits. The upper and lower limits may indicate thresholds or tolerances for the process. For example, if the actual trajectory of the process falls outside one of the limits, this may be a deviation that needs to be corrected.

Various factors may cause variations of the process. Some process variations are minor and may be ignored, other variations may be more serious, possibly resulting in a reduced quantity or purity of the product, or even in a product that is not usable. Process variations may relate to the environment (e.g., temperature or nutrient level) of the process. The multivariate process chart may be used to distinguish minor process variations from serious variations.

Conventionally, a multivariate process chart is determined from many process parameter values and process outputs of multiple processes. For example, a conventional multivariate process chart may be determined from thousands of online and offline process parameter values of at least three batch processes performed in a stirred tank reactor.

The multivariate process chart is conventionally calculated from a number of individual process trajectories. The multivariate process chart may include a golden batch trajectory as well as upper and lower limits. According to conventional approaches, a significant number of individual and separate processes may need to be carried out in a macroscale vessel in order to calculate the upper and lower limits around the golden batch trajectory. Further, frequent sampling may need to be conducted and physical samples may need to be analyzed via a scientific instrument (e.g., an analysis device such as a spectrometer). Such frequent sampling may be needed to obtain sufficient process data for determining the multivariate process chart. For example, the frequent sampling may include online process parameter values as well as offline process parameter values and process outputs.

The upper and lower limits of the multivariate process chart are conventionally determined based on the standard deviation of all the processes at each point of process maturity. The points of process maturity may be separated by specified periods of time. Process variations may arise in view of different control parameter values and development directions of each process. The variations may form a basis for the standard deviation or root mean square, which may be used as a basis for determining the upper and lower limits.

According to conventional approaches, the multivariate control chart may be determined from processes carried out in macroscale vessels having a working volume of over 10 L, or even over 1000 L. The costs of running such processes may be expensive, e.g., over € 100 000 or over € 200 000. Further, the processes may run for several days or even multiple weeks, and may require full time monitoring by trained personnel, incurring additional costs for personnel and facilities.

A first process control device (e.g., an automated bioreactor system) may be used as a platform to perform early process development on a first-scale (e.g., small or microscale, up to 1 L). More particularly, the process control device may be used to develop a biotechnology drug. After carrying out the process on the first-scale it may be desirable to transfer the process to a second (e.g., larger or macro) scale. At both the first-scale and the second-scale, the process should follow a general protocol and keep to a quality target product profile (QTPP).

When using the first process control device, the capability to create a multivariate process chart may be limited by the sampling frequency capability of the process control device. In particular, a robot of the process control device may need a certain amount of time to take individual samples from the first-scale vessels. For example, five minutes may be required for each sample and there may be twenty-four individual first-scale vessels. Accordingly, the maximum sampling frequency of the process control device per vessel is once every two hours. This may be too slow (i.e., there may not be enough samples) to create a multivariate process chart and to control the process effectively.

Accordingly, it is a problem to determine a multivariate process chart for use in controlling a process to produce a chemical, pharmaceutical, biopharmaceutical and/or biological product using a minimum of starting material. In particular, the volume of fluid for use in determining the multivariate process chart should be as small as possible. Further, the multivariate process chart should be determined quickly and with minimal labor cost, i.e., minimal resources should be required to monitor and control processes in order to determine the multivariate process chart.

Moreover, techniques disclosed in the present application may be particularly beneficial when the scientific instrument cannot be integrated into the process control device. More particularly, techniques disclosed in the present application may be particularly beneficial for making determinations with regard to process parameters that cannot be measured directly from the first-scale vessels. Such process parameters may include viable cell density (VCD) and nutrient (or metabolite) concentration. Integration of the scientific instrument into the vessels might not be possible in view of cost or size of the scientific instrument.

Hence, techniques disclosed in the present application may be particularly helpful when the time required for analysis in order to determine process parameter values is substantial in comparison to the time required to sample fluid from one of the first-scale vessels. In particular, some process parameter value determinations may take several minutes or more.

According to an aspect, a computer implemented method for controlling a process in a plurality of first-scale vessels via a first process control device is provided. Each of the first-scale vessels contains fluid. The process is for producing a chemical, pharmaceutical, biopharmaceutical and/or biological product. The method comprises receiving, by the first process control device, process parameters, the process parameters including process parameters to be controlled and process parameters to be measured.

In some cases, different conditions may be set for each of the first-scale vessels. In particular, a subset of the process parameters to be controlled (e.g., stirring speed and temperature) may be set differently for each one of the first-scale vessels. In particular, a design of experiments setup may be used to ensure that different process conditions are assessed. For example, about half of the process parameters to be controlled or between one third and one half of the process parameters to be controlled may be set differently for different ones of the first-scale vessels. The purpose of the variation of the process parameters to be controlled may be to discover the impact of variations in process parameters to be controlled on process outputs.

The method further comprises controlling, by the first process control device and at least partly in parallel, the process in each of the first-scale vessels. The process may be controlled at least partly in parallel in the sense that the process is started in a subset of the first-scale vessels before the process is started in another subset of the first-scale vessels. Similarly, it is possible that the process ends in a first subset of the first-scale vessels while continuing in a second subset of the first-scale vessels. Alternatively, it is possible that the process is controlled in all of the first-scale vessels in parallel.

The method further comprises periodically determining, prior to an assigning decision and at a first frequency, first sets of process parameter values for each of the process parameters from each of the first-scale vessels. The determining may be carried out, at least in part, by the first process control device. In particular, a scientific instrument, possibly implemented as an analysis device, may also be used in conjunction with the first process control device to determine the first sets of process parameter values.

The first sets of process parameters may include at least one nutrient level. The periodically determining may be carried out at a relatively low frequency. The determining may be carried out offline or atline. Further, the determining may be carried out using spectroscopy.

In the context of the present application, a low frequency (i.e., relatively low frequency) may be up to once per hour, or up to once every two hours. Determinations of values at the low frequency may be carried out offline or atline. A high frequency (i.e., relatively high frequency) may be at least once every two hours, at least once per hour or multiple times per hour. Determinations of values at the high frequency may be carried out online or inline. It is possible that ranges for the relatively low frequency and the relatively high frequency do not overlap.

The method further comprises carrying out the assigning decision by assigning corresponding ones of the first-scale vessels to an analysis subset and other ones of the first-scale vessels to an excluded subset. At least one vessel may be assigned to the analysis subset and at least one vessel may be assigned to the excluded subset. In some cases, between ¼ and ½ of the vessels may be assigned to the analysis subset and the rest of the vessels may be assigned to the excluded subset.

The method further comprises periodically determining, after the assigning decision and at a second frequency, second sets of process parameter values for each of the process parameters from the analysis subset of the first-scale vessels. The first frequency is different from the second frequency.

After the assigning decision, it may be that process parameter values are not determined from the excluded subset of the first scale vessels.

Steps involving periodically determining process parameter values may include directly or indirectly measuring values. The measuring may be carried out via a sensor (e.g., a temperature sensor). Alternatively, some determined values may be obtained or derived from other (measured or derived) values. In particular, determined values may be obtained via spectroscopy (e.g., using a scientific instrument).

The method further comprises controlling, by the first process control device and at least partly in parallel, the process in the first-scale vessels of the analysis subset according to the second sets of process parameter values.

Accordingly, the assigning decision may identify vessels that are performing well and these vessels may be assigned to the analysis subset. When the second frequency is greater than the first frequency, resources of the first process control device may be focused on determining process parameter values from the first-scale vessels in the analysis subset. By obtaining more process parameter values from the first-scale vessels in the analysis subset, control of the first-scale vessels in the analysis subset can be optimized. For example, if a nutrient (e.g., glucose) is being supplied to the first-scale vessels, then a higher frequency of process parameter value determinations may enable the control strategy for the nutrient to be optimized. This may result in the production of an improved product (e.g., with higher cell viability or purity).

In some cases, controlling according to the second sets of process parameter values comprises deriving a process output value from the second sets of process parameter values. A process output may be a key performance indicator (e.g., product titer) or a product specific (critical) quality attribute, CQA, (e.g., glycolisation profile). The method may further comprise initiating a control action via the first process control device in order to optimize the process output value. The control action may include increasing or decreasing supply of the nutrient.

According to another aspect, a computer implemented method for determining a multivariate process chart is provided. The multivariate process chart is to be used to control a process to produce a chemical, pharmaceutical, biopharmaceutical and/or biological product. The multivariate process chart includes a first trajectory, an upper limit for the first trajectory and a lower limit for the first trajectory. The method comprises providing a plurality of first-scale vessels, each of the first-scale vessels containing fluid for producing the product.

The fluid may include a medium and/or biological material (e.g., a cell line).

The method further comprises receiving, by a first process control device, process parameters, the process parameters including process parameters to be controlled and process parameters to be measured.

The process parameters to be controlled may be referred to as set points.

The method further comprises controlling, by the first process control device and at least partly in parallel, the process in each of the first-scale vessels. As discussed above, the process parameters to be controlled may be set differently for each of the first-scale vessels. More particularly, the process parameters to be controlled may be set in order to determine factors, such as values of the process parameters, that cause variations in process output values. Specifically, a design of experiments may be used in order to assess different process conditions and to determine a correlation between changes in process parameters and process outputs.

The method further comprises periodically determining, prior to an assigning decision and at a first frequency, first sets of process parameter values for each of the process parameters from each of the first-scale vessels. The method further comprises carrying out the assigning decision by assigning corresponding ones of the first-scale vessels to an analysis subset and other ones of the first-scale vessels to an excluded subset. The method further comprises periodically determining, after the assigning decision and at a second frequency, second sets of process parameter values for each of the process parameters from the analysis subset of the first-scale vessels. The first frequency is different from the second frequency. The method further comprises determining statistically representative values from the process parameter values of each of the first-scale vessels in the analysis subset. The method further comprises establishing the first trajectory from the statistically representative values. Moreover, the method comprises determining the upper limit and the lower limit based on a measure of variation of the process parameter values for the first-scale vessels in the analysis subset.

The assigning decision may be carried out at a transition between phases of the process, after a specified number of sets of process parameter values have been determined or at a specified time. Each phase of the process may indicate a change in the way the process is controlled. For example, the process may be a fed-batch process. Accordingly, the process may have an initial batch phase and a subsequent phase in which constant feeding of a substrate is carried out. The assigning decision may be carried out at the transition between the initial batch base and the subsequent phase. In one example, the entire process has a duration of fourteen days and the initial batch phase lasts three days.

The specified time may be predetermined. For example, the specified time may be at least ⅙ of a scheduled process duration or at least ⅕ of the scheduled process duration. The assigning decision may also be carried out after process parameter values have been determined from each of the first-scale vessels a specified number of times. For example, the assigning decision may be carried out after process parameter values have been determined from each of the first-scale vessels at least five times, at least ten times, at least fifteen times.

Each set of process parameter values may include values from each of the first-scale vessels. Further, a set of process parameter values may include values for each process parameter. Accordingly, if there are ten process parameters and ten first-scale vessels, then a set of process parameter values may include 100 values.

In some cases, the assigning decision is carried out according to at least one of the following criteria:
1. At least one of the process parameters is identified as a critical process parameter, and the first sets of values of the critical process parameter determined from one of the corresponding ones of the first-scale vessels are closer to a first specified value than the first sets of values determined from the other ones of the first-scale vessels. For example, level (or concentration) of a specific nutrient (e.g., glucose) may be identified as a critical process parameter. The first specified value may be a constant value at which the nutrient concentration should be maintained for the duration of the process.
2. Process output values determined from one of the corresponding ones of the first-scale vessels are closer to a second specified value than process output values determined from one of the other ones of the first-scale vessels. Accordingly, the periodically determining prior to the assigning decision may include determining process output values for each of the first-scale vessels. For example, viable cell density determined from one of the corresponding ones of the first-scale vessels may be closer to a target value (i.e., the second specified value) than process output values determined from one of the other ones of the first-scale vessels.
3. A predicted (i.e., estimated) trajectory for a corresponding one of the first-scale vessels is closer to a specified trajectory than a predicted trajectory for one of the other ones of the first-scale vessels. The specified trajectory may be a golden batch trajectory determined from average trajectories of all of the first-scale vessels or previously determined from average trajectories of another run of the process.
4. A multivariate score for one of the corresponding ones of the first-scale vessels is within an accepted range of the specified trajectory, wherein the multivariate score is derived from the first sets of process parameter values for the corresponding first-scale vessel. Accordingly, multivariate scores for the other ones of the first-scale vessels may be outside of the accepted range of the specified trajectory. The accepted range may include an upper limit and a lower limit of the specified trajectory.

The periodically determining may comprise collecting, by the first process control device, samples from at least one of the first-scale vessels. A sample may be collected from each one of the first-scale vessels in turn. The method further comprises analyzing, by a scientific (i.e., measuring) instrument, the samples. The scientific instrument may be implemented as an analysis device. The scientific instrument may be a substance or molecule identification instrument, i.e., a device capable of performing structural fingerprinting. The scientific instrument may be one of the following: a spectrometer, a mass spectrometer, a gel electrophoresis separation system, a chromatography system including a chromatograph for separation of analytes and a detecting instrument for qualitative and quantitative detection of the analytes after their separation.

In some cases, the periodically determining may be carried out via offline or atline analysis. More particularly, process parameter values determined directly by the first process control device may be excluded. Instead, the process parameter values may be obtained by the first process control device in conjunction with the scientific instrument.

The first sets of process parameter values and the second sets of process parameter values may include data directly determined by the first process control device and data determined, at least in part, by the scientific instrument. In other words, the first sets of process parameter values and the second sets of process parameter values may include data determined by the first process control device without using the scientific instrument (e.g., determined online or exclusively by the process control device) and data determined using the scientific instrument.

The first frequency and the second frequency may each be dependent on a capability of the first process control device. For example, the first process control device may require a specified sampling time to sample one of the first-scale vessels. The specified sampling time may be at least 5 minutes, at least 10 minutes, at least 15 minutes, or at least 20 minutes. Accordingly, when the specified sampling time is 5 minutes, and there are 24 of the first-scale vessels, then it may take two hours to sample all 24 vessels.

In some cases, the second frequency is greater than the first frequency. In particular, the second frequency may be at least about 10% greater, at least about 25% greater, at least about 50% greater or at least about 100% greater than the first frequency.

The magnitude of the second frequency may depend on how many of the first-scale vessels are in the analysis subset and how many of the first-scale vessels are in the excluded subset. Further, the capability may be a collecting and/or sampling speed. The capability may depend on one or more of the following: the number of vessels, a speed of the first process control device, other requirements of the first process control device relating to control of the process. The other requirements of the first process control device may include maintaining biological material (e.g., cultivating cells) in the first-scale vessels.

In general, the first process control device may have a number of tasks to perform. Sampling may be one of those tasks, however the frequency of sampling may depend on the resources of the process control device that are required to perform the other tasks. For example, the sampling resources of the first process control device available for periodically determining process parameter values from each of the first-scale vessels may be less than 25% of the sampling resources or less than 20% of the sampling resources. Sampling resources may include a robot (e.g., a controllable arm and a controller) for determining the process parameter values.

By focusing sampling resources of the first process control device on the first-scale vessels in the analysis subset, the first-scale vessels in the analysis subset can be sampled more frequently. This may enable process parameters and/or process outputs of the first-scale vessels in the analysis subset to be optimized. Such optimization may result in the production of a better quality product in the first-scale vessels of the analysis subset. In addition, the more frequent sampling of the first-scale vessels in the analysis subset may enable the determination of a multivariate process chart that can be more effectively used to control a process to produce the chemical, pharmaceutical, biopharmaceutical and/or biological product. More particularly, the multivariate process chart can be more effectively used on a second-scale that is larger than the first-scale.

In some cases, the method comprises determining a final set of process parameter values from each of the first-scale vessels in the excluded subset. Accordingly, it may be that after the assigning decision no further process parameter values are determined from the first-scale vessels in the excluded subset until the final set of process parameter values are determined. For example, when the assigning decision is carried out at the transition between phases of the process, process parameter values may be determined from vessels in the excluded subset before the transition and process parameter values may cease to be determined from the first-scale vessels in the excluded subset after the transition.

The final set of process parameter values may be used to update the design of experiments or validate the assigning decision. In particular, the final set of process parameter values may be used to determine whether the assigning decision was correctly carried out. In particular, the final set of process parameter values may confirm whether the process carried out in the vessels of the analysis subset produced a better product (e.g., a product meeting more success criteria) than the process carried out in the first-scale vessels of the excluded subset.

The step of periodically determining prior to the assigning decision may include determining process output values from each of the first-scale vessels. The step of periodically determining after the assigning decision may include determining process output values from the analysis subset of the first-scale vessels. Process outputs may be key performance indicators or product quality attributes (possibly critical quality attributes—CQAs).

The process outputs may include one or more of the following: quantity of product, quantity per unit volume of starting material, chemical composition of the product, purity of the product, amount of cell debris, amount of shear damage, starting material cost, energy cost for the process, glycosylation or glycan profile, charge variants, molecular weight variants, potency, aggregates, fragmentation, product titer, cell viability, agglomeration, protein sequence heterogeneity.

In some cases, it may be determined that one of the first-scale vessels in the analysis subset should be reassigned to the excluded subset, e.g., because the fluid in the vessel is not performing well (e.g., a process output such as VCD is below a specified value). Accordingly, periodically determining the second sets of process parameter values may further comprise determining, for each of the first-scale vessels in the analysis subset, a predicted (i.e., estimated) trajectory from the process parameter values of a corresponding one of the first-scale vessels. The predicted trajectory may also be based on process output values. When the predicted trajectory deviates from a specified trajectory by more than a tolerance value, reassigning the corresponding first-scale vessel from the analysis subset of the first-scale vessels to the excluded subset of the first-scale vessels. In this case, the specified trajectory may be a golden batch trajectory derived from the process parameter values determined from all of the first-scale vessels in the analysis subset. The tolerance value may be based on a standard deviation of process trajectories for all the first-scale vessels in the analysis subset.

Each of the first-scale vessels may have at least one of the following characteristics:
  it is a bioreactor or a microbioreactor,
  it includes stirring means for stirring its contents, the stirring means may be an impeller,
  it includes a gas delivery means, wherein the gas delivery means may include a sparge tube,
  it includes at least one sensor for measuring at least one of the following: pH, dissolved oxygen, temperature,
  it has a volume of at least 1 ml, at least 10 ml, at least 15 ml, up to 2000 L, up to 1000 L, up to 100 L, up to 50 L, up to 5 L, up to 1 L,
  it is disposable (i.e., single use).

According to another aspect, a computer implemented method for controlling a process to produce a chemical, pharmaceutical, biopharmaceutical and/or biological product using the multivariate process chart described above may be provided. The method comprises providing at least one second-scale vessel, the second-scale vessel containing fluid for producing the product, wherein a size (e.g., volume) of the second-scale vessel differs by at least one order of magnitude from a size of one of the first-scale vessels. The method further comprises receiving, by a second process control device, the process parameters. The method further comprises carrying out, by the second process control device, the following steps:
  controlling the process in the second-scale vessel,
  periodically determining process parameter values for the process parameters from the fluid in the second-scale vessel,
  estimating an actual trajectory of the process from the process parameter values, and
  when a deviation of the actual trajectory from the first trajectory exceeds the upper limit or the lower limit, controlling the process to correct the deviation, thereby influencing at least one of the process parameters.

According to yet another aspect, a computer program comprising computer-readable instructions is provided. The computer program may be implemented in a product (e.g., comprising a computer-readable medium). When loaded and executed on a computer system, the instructions cause the computer system to perform operations according to the method described above.

According to a further aspect, a process control device for controlling a process to produce a chemical, pharmaceutical, biopharmaceutical and/or biological product is provided. The process control device may correspond to the first process control device described above. The device comprises a plurality of first-scale vessels, each of the first-scale vessels being configured to contain fluid for producing the product. The device further comprises a robot capable of addressing each first-scale vessel, dispensing fluid to the first-scale vessels and extracting samples of fluid. The device further comprises a controller operable to receive process parameters, the process parameters including process parameters to be controlled and process parameters to be measured.

The controller is further operable to control, at least partly in parallel, the process in each of the first-scale vessels. The controller is further operable to periodically determine, prior to an assigning decision and at a first frequency, first sets of process parameter values for each of the process parameters from each of the first-scale vessels. The controller is further operable to carry out the assigning decision by assigning corresponding ones of the first-scale vessels to an analysis subset and other ones of the first-scale vessels to an excluded subset. The controller is further operable to periodically determine, after the assigning decision and at a second frequency, second sets of process parameter values for each of the process parameters from the analysis subset of the first-scale vessels. The first frequency is different from the second frequency. The controller is further operable to control, at least partly and parallel, the process in each of the first-scale vessels according to the second sets of process parameter values.

Steps described above as being optional for the computer implemented method aspects may also be applicable for the process control device.

According to yet another aspect, a process control device for determining a multivariate process chart is provided. The multivariate process chart is to be used to control a process to produce a chemical, pharmaceutical, biopharmaceutical and/or biological product. The multivariate process chart includes a first trajectory, an upper limit for the first trajectory and a lower limit for the first trajectory. The device comprises a plurality of first-scale vessels, each of the first-scale vessels being configured to contain fluid for producing the product. The device further comprises a robot capable of addressing each first-scale vessel, dispensing fluid to the first-scale vessels and extracting samples of fluid. The device further comprises a controller operable to receive process parameters, the process parameters including process parameters to be controlled and process parameters to be measured. The controller is further operable to control, at least partly in parallel, the process in each of the first-scale vessels. The controller is further operable to periodically determine, prior to an assigning decision and at a first frequency, first sets of process parameter values for each of the process parameters from each of the first-scale vessels. The controller is also operable to carry out the assigning decision by assigning corresponding ones of the first-scale vessels to an analysis subset and other ones of the first-scale vessels to an excluded subset. The controller is also operable to periodically determine, after the assigning decision and at a second frequency, second sets of process parameter values for each of the process parameters from the analysis subset of the first-scale vessels. The first frequency is different from the second frequency. The controller is also operable to determine statistically representative values from the process parameter values of each of the first-scale vessels in the analysis subset. The controller is also operable to establish the first trajectory from the statistically representative values. The controller is further operable to determine the upper limit and the lower limit based on a measure of variation of all the process parameter values for the first-scale vessels in the analysis subset.

According to an aspect, a computer implemented method for determining a multivariate process chart is provided. The multivariate process chart is to be used to control a process to produce a chemical, pharmaceutical, biopharmaceutical and/or biological product. The multivariate process chart includes a first trajectory, an upper limit for the first trajectory and a lower limit for the first trajectory. The multivariate process chart is derived from multiple variables, as opposed to a univariate process chart derived from a single variable. The term variable may be used to refer to a process parameter or a process output. The first trajectory may be a process trajectory reflecting an evolution of process parameter and process output values as the process matures (e.g., over time).

The method comprises providing a plurality of first-scale vessels, each of the first-scale vessels containing fluid for producing the product. The fluid may include starting material for the process. More particularly, the fluid may include a medium and/or biological material (e.g., a cell culture). The vessels may be controllable by a first process control device, more particularly, the vessels may be contained by the first process control device.

The method further comprises receiving, by the first process control device, process parameters, the process parameters including process parameters to be controlled and process parameters to be measured. The process parameters to be controlled (also referred to as set points or control set points) may constrain or regulate the process. Examples include temperature and stirring speed. Process parameters to be measured may be determined from samples of the fluid or via the first process control device. Examples include pH (measured from the process as opposed to a set point to be targeted) and nutrient level. A process parameter may be both a process parameter to be controlled and a process parameter to be measured, e.g., a temperature set point and a measured temperature.

The method further comprises controlling, by the first process control device and at least partly in parallel, the process in each of the first-scale vessels. The process may be controlled "at least partly" in parallel in the sense that the process might not start in each vessel at the same time. More specifically, the process may be performed in the same vessel multiple times or in different subsets of the vessels at different times. The process may also be controlled entirely in parallel.

The processes being carried out in each of the first-scale vessels may be designed to produce the same product.

The method further comprises periodically determining, at least in part by the first process control device, process parameter values for the process parameters from the fluid in each of the first-scale vessels. There may be at least 10, 20 or at least 40 vessels, preferably 12, 24 or 48 vessels, and periodically determining may be performed relatively infrequently (e.g., up to once per hour) for each vessel.

Periodically may refer to determining process parameter values according to specified time intervals. The specified time intervals may reflect limitations of the first process control device. In particular, determinations may be carried out based on how quickly the first process control device can extract samples from each of the vessels. Further, the speed at which process parameter values can be determined may be limited by other tasks that the first process control device needs to perform in order to ensure continuation of the processes in each of the vessels. In particular, the first process control device may be in continuous operation in order to control the environment in each of the first-scale vessels.

For example, the first process control device may need to perform various tasks in order to keep biological material viable (e.g., keep cell cultures alive) in the first-scale vessels. The other tasks required of the first process control device may limit the speed at which process parameter values can be determined from the fluid in each of the first-scale vessels. Thus, 4-6 hours may be required to determine process parameter values for all the vessels, such that only 4-6 sets of process parameter values can be determined in a single day.

Accordingly, it may be a problem to determine a multivariate process chart from a limited number of process parameter values.

The method may further comprise defining groups of (or within) the process parameter values according to a common characteristic, wherein each of the groups includes process parameter values determined from multiple ones of the first-scale vessels. The groups may be defined after sufficient data has been collected from each of the process parameter vessels. For example, the groups may be defined after each of the vessels has been accessed by the first process control device. Alternatively, each of the first-scale vessels may be accessed a specified number of times before the groups are defined.

Defining the groups of process parameter values may include generating a batch evolution model from the process parameter values. Each of the groups may be a subset (e.g., a proper subset) of the process parameter values. The groups of the process parameter values may be defined after each of the processes has been run until completion.

Rather than the individual process parameter values, the groups may include multivariate scores derived from the process parameter values, where each of the scores represents multiple process parameter values. The multivariate scores may be determined according to a multivariate statistical process control technique, such as principal component analysis (PCA) and/or multi-way partial least squares (PLS) regression.

The method further comprises determining at least one statistically representative value for each of the groups of process parameter values. The method further comprises establishing the first trajectory from the statistically representative values. Establishing the first trajectory may include interpolating the statistically representative values. The interpolation may be spline interpolation.

The method further comprises determining the upper limit and the lower limit based on a measure of variation within each group.

Different conditions may be set for each of the first-scale vessels. In particular, a subset of the process parameters to be controlled (e.g., stirring speed and temperature) may be set differently for each one of the first-scale vessels. In particular, a design of experiments setup may be used to ensure that different process conditions are assessed. For example, about half of the process parameters to be controlled or between one third and one half of the process parameters to be controlled may be set differently for different ones of the first-scale vessels. The purpose of the variation of the process parameters to be controlled may be to discover the impact of variations in process parameters to be controlled on process outputs.

In some cases, data obtained from one or more of the first-scale vessels may be excluded. More particularly, the method may comprise selectively excluding process parameter values determined from respective values of the first-scale vessels in order to identify remaining process parameter values. Thus, the process parameter values that are not selectively excluded are identified as the remaining process parameter values.

The groups of the process parameter values may consist of (i.e., are exclusively limited to) the remaining process parameter values. The selective exclusion of process parameter values may depend on characteristics of the process in each of the first-scale vessels. For example, process parameter values obtained from one of the respective ones of the first-scale vessels may differ significantly from process parameter values obtained from other ones of the first-scale vessels.

The remaining process parameter values may be identified when at least one of the following criteria (i)-(v) applies:
  (i) Process parameter values determined from one of the respective ones of the first-scale vessels are identified as outliers in comparison to process parameter values determined from the other first-scale vessels. For example, in the context of batch processing, process parameter values from a batch in one of the first-scale vessels may be compared to process parameter values from the other batches or to process parameter values of a golden batch. In this context, a batch evolution model may be used to organize the process parameter values and as a basis for comparison.
  (ii) At least one of the process parameters is identified as a critical process parameter, and at least one value of the critical process parameter determined from one of the respective ones of the first-scale vessels is outside an accepted range. For example, if dissolved oxygen is determined to be a critical process parameter and values of dissolved oxygen determined from a respective one of the first-scale vessels are below a lower limit of the accepted range, than all values for the respective one of the first-scale vessels may be selectively excluded.
  (iii) Process output values determined from one of the respective ones of the first-scale vessels are outside an accepted range. This may be a univariate decision; in particular, values of only one process output might be enough for the decision. For example, cell viability, viable cell density, or product titer may be considered at day 3 of the process. If values of one of these process outputs is outside a specified range on day 3, then the respective one of the first-scale vessels for which the process output values were measured may be selectively excluded. For cell viability, the specified range may be below 90%, for viable cell density the specified range may be less than 5 million cells per mL, and for product titer the specified range may be less than 0.5 grams/L.
  (iv) A predicted first trajectory for one of the respective ones of the first-scale vessels is more than a specified distance from a golden batch trajectory for the first-scale vessels (i.e., a mean of the trajectories of the first-scale vessels) or a nearest neighbor of the respective one of the first-scale vessels. The nearest neighbor may refer to the first-scale vessel having a predicted trajectory closest to the respective one of the first-scale vessels.
  (v) A multivariate score for one of the respective ones of the first-scale vessels is outside an accepted range or more than a specified distance from the golden batch trajectory, wherein the multivariate score is derived from process parameter values and/or process output values of the respective ones of the first-scale vessels.
  For example, the multivariate score may be derived from a combination of process outputs, e.g., a combination of cell viability, viable cell density, and product titer. As another example, the multivariate score may be derived from a combination of at least one process parameter and at least one process output, more specifically, the multivariate score may be based on dissolved oxygen and viable cell density. The multivariate score may be derived using one of the multivariate statistical process control techniques (MSPC) mentioned above or another MSPC technique, such as DModX (also called distance to the model), or Hotellings $T^2$ distribution (combining the scores of all components, e.g., PCA components).

In the context of the present application, an "accepted range" may have only one limit, e.g., greater than 50% purity could be the accepted range.

The selective exclusion of process parameter values from respective ones of the first-scale vessels may be performed using various multivariate statistical process control techniques including or other techniques. Further, other trajectories may also be used, e.g., determined from a different process control device or from a different usage of the first process control device.

In some cases, one or more of the following (i)-(ii) may apply:
  (i) Process parameter values for one of the process parameters are determined at a different process maturity than other process parameter values for another one of the process parameters. For example, one scientific instrument (e.g., a chemistry, fermentation or nutrient analyzer) may determine process parameter values for a metabolite process parameter at a different time than a different scientific instrument (e.g., a spectrometer) is used to determine nutrient levels (e.g., glucose levels). Process maturity may refer to time or a stage of development of the process. Thus, different process maturities may refer to different times or different stages of development.
  (ii) Process parameter values for one of the first-scale vessels are determined at a different process maturity than process parameter values for another one of the first-scale vessels. For example, a sample from one of the first-scale vessels may be taken at a different process maturity than a sample for another one of the first-scale vessels. Process parameter values may be determined from each of the samples.

In some cases, the common characteristic is one of the following:
  A time interval during which the corresponding group of process parameter values was determined.
  A value of a process output determined from the same first-scale vessel as the corresponding group of process parameter values. For example, a plurality of process outputs may be periodically determined from the first-scale vessels. More specifically, a percentage of viable cells may be determined as a process output every six hours from each of the first-scale vessels. Accordingly, process parameter values determined from first-scale vessels having a first process output value (e.g., a first percentage of viable cells) may be in a first group, whereas process parameter values determined from first-scale vessels having a second process output value (e.g., a percentage of viable cells) may be in a second group. The first process output value may be within a first specified range and the second process output value may be within a second specified range. The first specified range may overlap with the second specified range.

A range of values for one of the process parameters. For example, the process parameter may be nutrient concentration, and a first group may include process parameter values determined when the nutrient concentration has a specified value. Similarly, a second group of process parameter values may include values determined when the nutrient concentration has a second specified value. The specified values may each be within different, possibly overlapping, ranges of values.

Each of the groups of process parameter values may correspond to a different range and the ranges may overlap.

The common characteristic reflects a process maturity, i.e., a degree or level of process maturity. In particular, groups may be defined according to similar process maturity. In other words, process parameter values may be grouped according to process maturity (e.g., the time at which the values were determined).

The time interval may correspond to a duration required for the first process control device to obtain a sample of fluid from each one of the first-scale vessels. The time interval may also correspond to the additional time required to determine process parameter values from the fluid. More particularly, a first group may be defined from process parameter values determined from a first set of samples, including a single sample from each one of the first-scale vessels. Further, groups may be defined using a technique for smoothing out localized fluctuations in the process parameter values. More particularly, groups may be defined using a moving average. Accordingly, a first value obtained from a first one of the first-scale vessels may be excluded from the second group and a second value determined from the first one of the first-scale vessels may be added. In other words, adjacent groups may be formed by shifting forward, i.e., excluding a first process parameter value determined from one of the first-scale vessels and including a next value determined from the same one of the first-scale vessels. Other smoothing techniques could also be applied, e.g., interpolation. Further, weighting may be applied to more recently obtained values e.g., by giving those values a higher weight, or by giving a lower weight to values that deviate substantially from other process parameter values.

In some cases, the at least one statistically representative value is determined from a mean or average of a corresponding group of the process parameter values. Moreover, as discussed above, at least one multivariate score may be determined from process parameter values within a group before determining the statistically representative value. Accordingly, the statistically representative value may be a mean of process parameter values within a group or from a mean of scores derived from process parameter values of the group.

Establishing the first trajectory may comprise calculating a moving average of the process parameter values (or multivariate scores derived from the process parameter values) and/or interpolating values at time points that are not represented in the process parameter values. In particular, because the process parameter values may not be equally distributed, interpolation might be needed to fill in gaps between process parameter values.

The measure of variation may be based on a standard deviation. In particular, the measure of variation may be calculated for each group and may be based on a standard deviation within the group. The upper limit and the lower limit may be determined as a function of the standard deviation from the first trajectory (e.g., about 3 times the standard deviation). In some cases, the upper limit and the lower limit may be determined based on characteristics of the process. For example, in some processes there may be a higher tolerance for error than in other processes; a greater multiple of the standard deviation may be used when there is a higher tolerance for error, whereas a lesser multiple of the standard deviation may be used when there is a lower tolerance for error. Determining the upper limit and the lower limit may comprise calculating a moving average of the standard deviation from the first trajectory and/or interpolating values for the standard deviation at time points that are not represented in the process parameter values.

As an alternative to the standard deviation, the upper and lower limits may be based on a root mean square of a univariate score (e.g., an average) for a process parameter and a corresponding point on a golden batch trajectory for the process. Interpolation, e.g., spline interpolation, may be used to smooth the upper and lower limits.

In addition, outlier detection within each group may be performed. In particular, before determining the upper and lower limits, outliers within each group may be identified and eliminated so that they do not unduly affect the determination. Outliers may be detected via comparison with a median within the group.

Each of the first-scale vessels may have at least one of the following characteristics:
  it is a bioreactor or a microbioreactor,
  it includes stirring means for stirring its contents, wherein the stirring means may be an impeller or agitator,
  it includes a gas delivery means, wherein the gas delivery means may include a sparge tube,
  it includes at least one sensor for measuring at least one of the following: pH, dissolved oxygen, temperature,
  it has a volume of at least 1 ml, at least 10 ml, at least 15 ml, up to 2000 L, up to 1000 L, up to 100 L, up to 50 L, up to 5 L, up to 1 L,
  it is disposable (i.e., single use).

More specifically, the first-scale vessels may be microscale vessels having a volume (i.e., a working volume) of between 1 ml and 10 L, preferably between 10 ml and 2 L, more preferably between 15 ml and 250 ml. The first-scale vessels may be made from glass or plastic. In particular, the first-scale vessels may be made from a thermoplastic, for example, polystyrene or polycarbonate. The first-scale vessels may each include one or more sensors, e.g., sensor spots. The sensors may be used to determine process parameter values, e.g., temperature, dissolved oxygen and/or pH.

Process parameter values may also be determined using an analysis module. The analysis module may be part of the first process control device or an extension (i.e., add-on) to the first process control device. The analysis module may be used to determine process parameter values such as pH and glucose. pH values determined via the analysis module may be used as reference measurements to adjust sensors in the first scale vessels.

The stirring means may be implemented as a pitch blade or a Rushton impeller. A drive mechanism may be used to drive the stirring means in each of the first-scale vessels.

Periodically determining the process parameter values for the process parameters may comprise collecting, by the first process control device, samples from a plurality of the first-scale vessels. More particularly, the determining may be carried out by extracting samples via the process control device and analyzing the samples, possibly via another device. In some cases, samples may be collected from all of the first-scale vessels.

In addition, the periodically determining may further comprise analyzing, by a scientific instrument, the samples. The scientific instrument may be a substance or molecule identification instrument, i.e., a structural (or spectral) fingerprinting device. The scientific instrument may be a chemistry or fermentation analyzer, or a measuring instrument (e.g., for measuring nutrients and/or metabolites).

The scientific instrument may be one of the following: a spectrometer, a mass spectrometer, a gel electrophoresis separation system, a chromatography system including a chromatograph for separation of analytes and a detecting instrument for qualitative and quantitative detection of the analytes after their separation.

Periodically determining the process parameter values may be carried out offline or atline. In particular, the process parameter values may be limited to those obtained via analysis by the scientific instrument. For example, structural fingerprinting may be carried out via Raman spectroscopy. Sampling for Raman spectroscopy may require 15 minutes per vessel. Accordingly, a determination may be made for 24 vessels in 6 hours. In the course of the determination, each vessel of the process control device may be accessed.

Determining the process parameter values via the scientific instrument (e.g., structural fingerprinting device) may have the advantage that all parameters are measured in the same units. Further, parameter values may be determined for multiple process parameters (or all process parameters) at the same (or nearly the same) time from a single sample, without placing an undue burden on the first process control device. The process parameter values determined via the scientific instrument may be a subset of sampling-dependent process parameters, which are discussed in more detail below.

The scientific instrument may also be implemented as an analysis device (e.g., a chemistry, fermentation or nutrient analyzer). The analysis device may involve the use of radiofrequency impedance spectroscopy to measure specific capacitance of the fluid. In particular, the analysis device may measure specific capacitance of a culture medium and/or cells within the fluid.

The first process control device may include a robot, a steering device for the robot and a controller. The robot may be activated to control the process and to periodically determine process parameter values. The robot may be capable of performing at least the following tasks: addressing each first-scale vessel, dispensing fluid to the first-scale vessels, and extracting samples of fluid from the first-scale vessels.

The robot may be capable of extracting a sample of fluid from each of the first-scale vessels at least once every other day, at least once per day, at least twice per day, at least four times per day, at least six times per day, at least twelve times per day.

The first process control device may include at least one of the following:
an automated pipetting system,
a workstation for specifying the control parameters and monitoring the process.

The automated pipetting system may be part of a sampling device, where the sampling device is in turn part of the first process control device.

The workstation may be implemented as a process control module.

Limitations on the speed of extracting samples may arise because of demands on the first process control device (e.g., the robot) with regard to controlling the process (e.g., keeping biological material in the first-scale vessels viable).

Accordingly, a speed of periodically determining the process parameter values for the process parameters may depend on a capability of the first process control device. In particular, the speed at which process parameter values are determined may depend on the number of vessels and/or tasks associated with keeping biological material viable (e.g., cultivating cells) in the first-scale vessels. Thus, the first process control device may need to ensure that cells remain alive within the first-scale vessels in addition to collecting samples and this may involve a number of tasks requiring significant resources.

The process parameters to be controlled and the process parameters to be measured may each include one or more of the following: dissolved oxygen (DO), dissolved carbon dioxide, pressure, pH, flow rates, temperature, nutrient level, stirring speed, substrate concentration (e.g., glucose, glutamine), metabolite concentration (e.g., ethanol, glycerol), oxidation reduction potential, turbidity. The flow rates may include carbon dioxide, oxygen and acids/bases. The nutrient level may refer to organic nutrients (e.g., yeast extract) or inorganic nutrients (e.g., trace minerals).

The values of the process parameters may include time series values.

The control parameters (i.e., process parameters to be controlled or set points) may also include basal set points. The control parameters may be set at the beginning of the process and controlled throughout the process in order to control the environment within the first-scale vessels. The control parameters may vary among different ones of the first-scale vessels.

The terms offline, atline and online may refer to the frequency at which process parameter values are determined from the fluid in the first-scale vessels. The term offline may also indicate that analysis of the fluid is, at least in part, performed remotely from the first process control device, e.g., in a laboratory. For example, a sample obtained offline may be transferred to the laboratory for time delayed analysis. Offline measurements may be carried out less than once per hour, e.g., twice per day.

Atline measurements may be performed at a frequency similar to offline measurements. Determination of process parameter values atline may be carried out in closer proximity to the first process control device in comparison to process parameter values determined offline.

Online determination of process parameter values may be carried out with greater frequency than atline or offline determination of process parameter values. For example, online measurements may be performed more than once per hour, more than three times per hour, or about sixty times per hour. Online measurements may be carried out in situ or ex situ. In situ measurements might not involve removing a sample from the vessel. Instead, a sensor (e.g., a temperature or pH sensor spot) may be directly inserted into the vessel or separated from the vessel by a wall. Another possible in situ configuration involves a sampling loop with one online sensor, a non-destructive online analyzer and return of a sample to the vessel after analysis. In online ex situ sampling, the sample may be transported to an online analyzer and does not return to the vessel after analysis.

The process parameters may include one or more of the following:
- at least one sampling-dependent process parameter, such as nutrient level/concentration, osmolality,
- at least one sampling-independent process parameter, such as pH, DO, stirring speed,
- at least one scale-independent process parameter, such as temperature,
- at least one scale-dependent process parameter, such as stirring speed.

The process parameters may be limited to sampling-dependent process parameters.

In addition, the process parameters may be limited to offline and/or atline process parameters (i.e., excluding online process parameters). Limiting the process parameters in this way may make it easier to analyze the process parameter values more quickly. In particular, limiting the process parameter values in this way may enable the multivariate process chart to be determined more efficiently. The efficiency may be realized because fewer resources are required to perform the analysis.

A sampling-dependent process parameter may refer to a process parameter that is measured via sampling. In particular, determining a sampling-dependent process parameter value may require sampling fluid from one of the first-scale vessels. A sampling-independent process parameter does not require sampling. For example, determining a sampling-independent process parameter value may involve remotely interrogating a sensor spot of the first-scale vessel.

A scale-independent process parameter may have a value that is independent of the scale of the process. Accordingly, the same value for the scale-independent process parameter can be expected at the first-scale and at a second-scale that differs by at least order of magnitude from the first-scale. A scale-dependent process parameter may vary between different scales. Accordingly, values of a scale-dependent process parameter may differ between the first-scale and the second-scale.

According to another aspect, a computer program comprising computer readable instructions is provided. The instructions, when loaded and executed on a computer system, cause the computer system to perform operations as described above. The computer program may be implemented in a product, e.g., tangibly embodied in a computer readable medium.

According to yet another aspect, a process control device for determining a multivariate process chart is provided. The multivariate process chart is to be used to control a process to produce a chemical, pharmaceutical, biopharmaceutical and/or biological product. The multivariate process chart includes a first trajectory, an upper limit for the first trajectory and a lower limit for the first trajectory.

The device comprises a plurality of first-scale vessels, each of the first-scale vessels being configured to contain fluid for producing the product. The device further comprises a robot capable of addressing each first-scale vessel, dispensing fluid to the first-scale vessels, and extracting samples of fluid from the first-scale vessels.

The device further comprises a controller operable to receive process parameters, the process parameters including process parameters to be controlled and process parameters to be measured. The controller is further operable to control, at least partly in parallel, the process in each of the first-scale vessels. The controller is further operable to cause process parameter values to be periodically determined for process parameters from the fluid in each of the first-scale vessels. The controller is further operable to define groups of the process parameter values according to a common characteristic, wherein each of the groups includes process parameter values determined from multiple ones of the first-scale vessels. The controller is further operable to determine at least one statistically representative value for each of the groups of process parameter values. The controller is further operable to establish the first trajectory from the statistically representative values. The controller is further operable to determine the upper limit and the lower limit based on a measure of variation within each group.

The process control device may be capable of managing at least 4 vessels, at least 8 vessels, at least 12 vessels, at least 16 vessels, at least 24 vessels or at least 48 vessels. Multiple ones of the vessels may be grouped in stations, e.g., culture stations.

The controller may be capable of controlling (i.e., managing) individual environments in each of the first-scale vessels. In particular, the controller may be capable of controlling one or more of the following parameters in each of the vessels: pH, temperature, dissolved oxygen, nitrogen, carbon dioxide. In addition, the controller may be capable of controlling stirring speed for each of the first-scale vessels.

The process control device may include a gas analyzer (e.g., a mass spectrometer) for measuring carbon dioxide and/or oxygen. The gas analyzer may also be capable of measuring an oxygen update rate, a carbon dioxide emission rate, a respiration quotient. The process control device may include sensing means (e.g., optochemical sensor spots), gas delivery means (e.g., a sparge tube) and stirring means (e.g., a pitch blade or Rushton impeller). The process control device may be capable of managing processes in each of the first-scale vessels simultaneously, i.e., in parallel. The process control device may be capable of controlling nutrient levels within the first-scale vessels. The process control device may be capable of communicating samples to one or more scientific instruments, e.g., molecule identification instruments, such as a spectrometer.

According to yet another aspect, a computer implemented method for controlling a process to produce a chemical, pharmaceutical, biopharmaceutical and/or biological product using the multivariate process chart described above is provided. The method comprises providing at least one second-scale vessel, the second-scale vessel containing fluid for producing the product. A size (i.e., volume) of the second-scale vessel differs by at least one order of magnitude from a size (i.e., volume) of one of the first-scale vessels. For example, the size of the second-scale vessel may be at least one order of magnitude greater than the size of one of the first-scale vessels. Accordingly, if the first-scale vessels each have a volume of 250 ml, then a volume of the second-scale vessel may be at least 1 L (or more particularly, at least 2.5 L). The sizes may differ by multiple orders of magnitude, such that the size of each of the first-scale vessels may be 15 ml while the size of the second-scale vessel may be 200 L.

The method further comprises receiving, by a second process control device, the process parameters. The second process control device may be operable to control an environment within the second-scale vessel. The method further comprises carrying out by the second process control device the following steps:
- controlling the process in the second-scale vessel, periodically determining process parameter values for the process parameters from the fluid in the second-scale vessel, estimating an actual trajectory of the process from the process parameter values, and when a deviation of the actual trajectory from the first trajectory exceeds the upper limit or the lower limit, controlling the process to correct the deviation, thereby influencing at least one of the process parameters.

As discussed above, the actual trajectory is a process trajectory of the process being controlled.

The multivariate process chart may be adapted for use with the second-scale vessels. In particular, parameter values for scale-dependent parameters may be adapted using a transfer function. Accordingly, values for at least one of the process parameters may be adapted via the transfer function for the second-scale vessel. The transfer function may be bijective. The process parameters that are adapted may be scale-dependent process parameters. The transfer function could be a mathematical function, mechanistic model, statistical model or a combination thereof, or any computational relationship between a first vessel function and a second vessel function. The transfer function may take various forms. In particular, the transfer function may be Gaussian or a wavelet transform. Polynomial, exponential, logarithmic, or linear transfer functions could also be used.

A condition may include at least one process output and/or at least one process parameter. When the process produces a product meeting the condition and the actual trajectory is outside the upper limit or the actual trajectory is outside the lower limit, the method may comprise updating the corresponding limit (i.e., the upper limit or the lower limit) according to the actual trajectory.

Each of the process outputs is a product quality attribute or a key performance indicator. Process outputs may be distinguished from process parameters in that process parameters can be directly influenced or controlled (e.g., a temperature process parameter may be directly controlled by increasing the temperature in a vessel), whereas process outputs might not be directly controllable. Instead, process outputs may be indirectly influenced by controlling process parameters.

Further details and examples regarding process outputs, key performance indicators and product quality attributes can be found in "Cell culture processes for monoclonal antibody production", Feng Li et al., 2010.

The process outputs may include one or more of the following: a total quantity of product, quantity per unit volume of input fluid or starting material, a specified characteristic, such as the chemical composition of the product, purity of the product, starting material cost, energy cost for the process, glycosylation or glycan profile, charge variants or isoforms, including acidic and basic variants, low molecular weight variants, potency or biological activity, aggregates or aggregation level, fragmentation.

The multivariate control chart, or possibly an underlying batch evolution model of the multivariate control chart, may be validated at the second-scale. Process parameter values determined at the second-scale may include online process parameter values in addition to offline process parameter values. Further, process parameters received by the second process control device may include sampling-independent process parameters in addition to sampling-dependent process parameters. Accordingly, process parameters received by the first process control device may be limited to sampling-dependent process parameters, whereas process parameters received by the second process control device may include sampling-dependent process parameters and sampling-independent process parameters.

Process parameter values may be determined differently at the second-scale in comparison to the first-scale. In particular, atline Raman spectroscopy and a flow cell may be used to determine some or all of the process parameter values at the first-scale, while an inline immersion probe along with atline analysis devices may be used to determine process parameter values at the second-scale.

If the actual trajectory is outside the upper or the lower limit of the multivariate process chart, the transfer function may be updated in order to correct for the deviation.

The subject matter described in this application excludes treatment of the human or animal body by surgery or therapy, and diagnostic methods practiced on the human or animal body.

The subject matter described in this application can be implemented as a method or on a device, possibly in the form of one or more computer programs (e.g., computer program products). Such computer programs may cause a data processing apparatus to perform one or more operations described in the application.

The subject matter described in the application can be implemented in a data signal or on a machine readable medium, where the medium is embodied in more or more information carriers, such as a CD-ROM, a DVD-ROM, semiconductor memory, or a hard disk.

In addition, the subject matter described in the application can be implemented as a system including a processor, and a memory coupled to the processor. The memory may encode one more programs to cause the processor to perform one or more of the methods disclosed in the application. Further subject matter described in the application can be implemented using various machines.

DETAILED DESCRIPTION

In the following text, a detailed description of examples will be given with reference to the drawings. Various modifications to the examples may be made. In particular, one or more elements of one example may be combined and used in other examples to form new examples.

Figure 1:
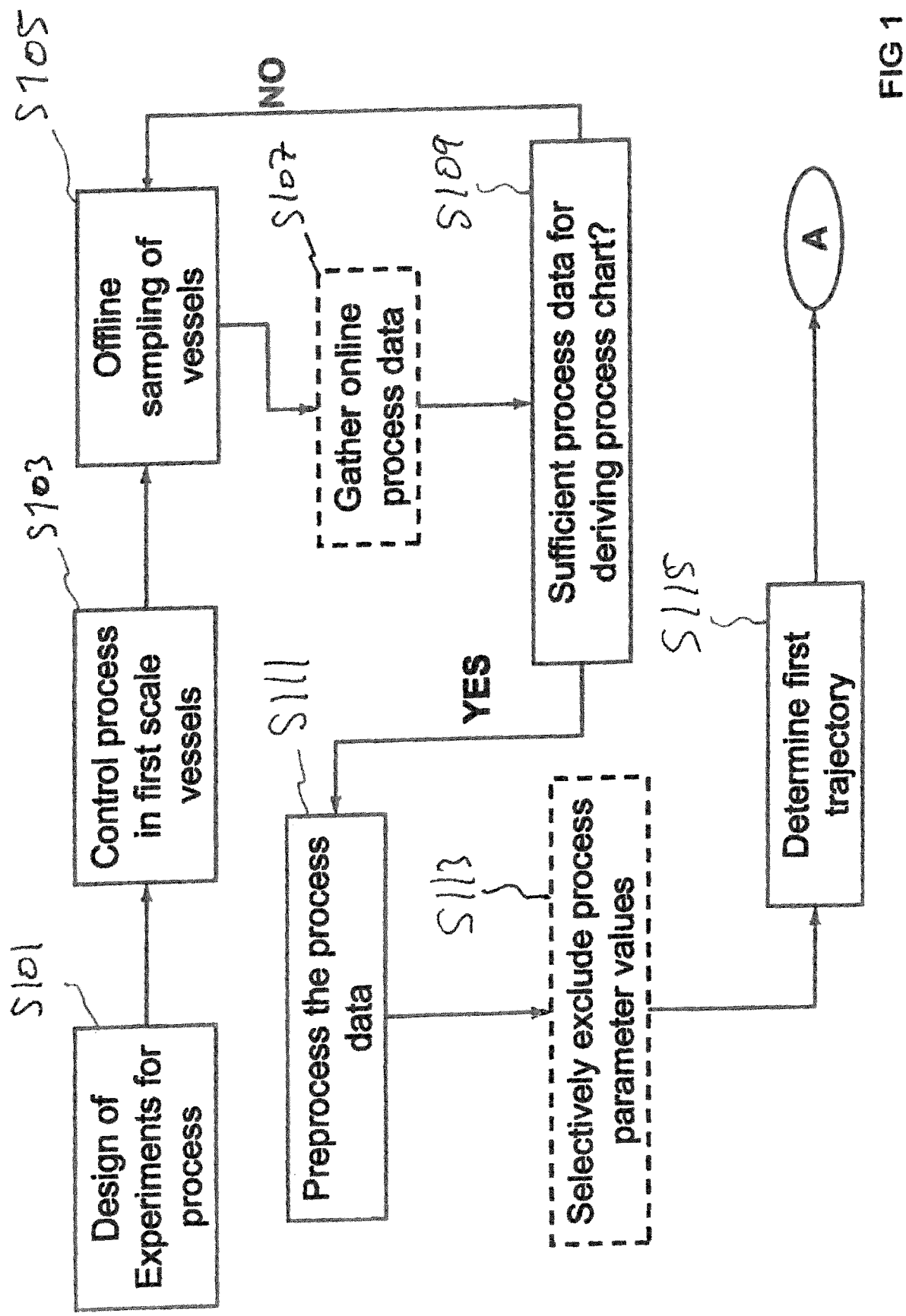
FIG. 1 shows steps of a method for determining a multivariate process chart.

FIG. 1 shows steps S101 to S115 of the method for determining the multivariate process chart.

At step S101, a plan or design for determining a multivariate process chart may be developed. In particular, a first process control device receives process parameters. The first process control device provides a plurality of first-scale vessels, each of the first-scale vessels containing fluid for producing a product. According to the plan, a subset of the process parameters received by the first process control device may be identified as variables to be varied. The variables may be varied according to design of experiments conditions.

More particularly, it may be that process parameters influencing process outputs have been identified through a screening process and that testing has already been carried out to determine ways that the identified process parameter values influence process outputs in an optimization process. Accordingly, at step S101, the plan for determining the multivariate process chart may be developed in the context of robustness testing with regard to the sensitivity of the process outputs to changes in the identified process parameters. Accordingly, the design of experiments may describe controlled variations of the process parameters for determining an upper limit and a lower limit of the multivariate process chart. Further details regarding design of experiments and its use in determining how parameters (factors) and outputs (responses) relate to each other may be found in "Design of Experiments—Principles and Applications", L. Eriksson, E. Johansson, N. Kettaneh-Wold, C. Wikström, and S. Wold, 2008.

At step S103, the process is controlled, by the first process control device and at least partly in parallel, in each of the first-scale vessels. Parameters to be controlled for each of the first-scale vessels may be varied according to the plan determined in step S101. The process may be started and ended in each of the first-scale vessels at the same time, so that the process is controlled in each of the first-scale vessels entirely in parallel. Alternatively, the process may be staggered for different ones of the first-scale vessels, such that, for example, the process starts at a first time and ends at a second time for a first subset of the first-scale vessels and starts at a third time and ends at a fourth time for a second subset of the first-scale vessels. In such a case, the process would be controlled in the different subsets partly in parallel but not entirely.

The first-scale may range from approx. 1 ml to approx. 1 L in volume.

Step S105 includes periodically determining, at least in part by the first process control device, process parameter values for the process parameters from the fluid in each of the first-scale vessels. The process parameter values may be determined at a relatively low frequency. Step S105 may be carried out via sampling of the fluid in the first-scale vessels. Analysis of the samples may be performed offline and/or atline. Some or all of the process parameters to be measured may be determined at step S105. In some cases (e.g., basic fermentation), there may be a relatively low number of process parameters, possibly as few as 3 process parameters, e.g. pH, dissolved oxygen, temperature. In other cases there may be up to several hundreds to thousands of process parameters, e.g., in cases involving data from the scientific instrument, particularly, spectroscopy or chromatography data, or combinations thereof.

Step S105 may be carried out via a scientific instrument (e.g., a measurement device). In particular, samples extracted or collected by the first process control device may be analyzed by the scientific instrument. The scientific instrument may be a structural fingerprinting device or an analysis device (e.g., a chemistry analyzer). In particular, a spectrometer or cell counter may be used to determine process parameter values.

The determination of the process parameter values may be carried out at least in part by the first process control device, in the sense that samples may be extracted by the first process control device and analysis of the samples may be performed by a scientific or instrument separate from the first process control device. The scientific or measuring instrument may also be part of the first process control device. Accordingly, the determination of the process parameter values may be carried out entirely by the first process control device.

The determination of the process parameter values may be carried out exclusively for the process parameters to be measured. One or more of the process parameters, e.g., temperature, may be both process parameters to be controlled and process parameters to be measured.

Process parameter values may be determined exclusively at the low frequency, e.g., offline or atline. Alternatively, at step S107, process parameter values may also be determined at a high frequency, e.g., online or inline. The online or inline process parameters values may be determined as time series or interpolated data. In particular, values for at least one of the process parameters may be determined at a relatively high frequency. The online process parameter values may be determined as frequently as at least once per hour or even at least once per second.

Examples of process parameters whose values are determined at the high frequency include pH, dissolved oxygen, carbon dioxide, and stirring speed. Examples of relatively infrequently determined (e.g., offline or atline) process parameters include viable cell density, metabolite concentration, osmolality, and product titer.

At step S109, it may be established whether there is sufficient process data (i.e., process parameter values) to determine the multivariate process chart. The determination may be made in a number of ways. For example, the determination may be made after a specified amount of time, such as at least three days or at least five days. Alternatively, the determination may be made after specified number of samples have been collected from the first-scale vessels, e.g., 10 samples in total. As yet another alternative, the determination may be made after a specified number of samples have been collected from each vessel, for example, at least one from each vessel, at least three from each vessel, or at least five from each vessel, other criteria may also be used. If there is insufficient process data, step S105 may be carried out again. Further, step S107 may be carried out for the first time or repeated.

At step S111, the process data (i.e., the process parameter values) may be preprocessed. The preprocessing may include carrying out interpolation, filtering or smoothing of the data. The smoothing may include carrying out a moving average and/or a weighted average. Further, outliers may be detected and given a lower weight or eliminated. Preprocessing may be particularly useful for process parameters that have a relatively high tolerance for error. For example, the scientific instrument may only be capable of determining viable cell density to within ±10%.

Step S113 includes selectively excluding process parameter values determined from respective ones of the first-scale vessels in order to identify remaining process parameter values. Step S113 might only be performed in certain cases. For example, the process parameter values may be evaluated in various ways (e.g., as described below) to determine significant deviations. If significant deviations are determined then process parameter values (e.g., from selected first-scale vessels) may be excluded. Alternatively, if no significant deviations from a standard or average are determined, then it is possible that no process parameter values would be selectively excluded. Process parameter values that are not selectively excluded are referred to as remaining process parameter values.

Selectively excluding process parameter values may include deriving a batch evolution model from the process parameter values. Accordingly, the batch evolution model may be used to determine whether process parameter values from one or more of the first-scale vessels can be identified as outliers in comparison to process parameter values determined from the other first-scale vessels. For example, process parameter values determined from one of the first-scale vessels may be compared to the batch evolution model as a whole. If process parameter values from the first-scale vessel are very different or not in the batch evolution model, then those values may be selectively excluded.

Selective exclusion may also be carried out according to a univariate decision. For example, a variable such as a process parameter or a process output may be identified as a basis for the univariate decision. If a value of the identified process parameter or process output is found to be outside an accepted range at a specified process maturity (e.g., a specified duration or period from the start of the process) then process parameter values determined from that first-scale vessel may be selectively excluded.

In addition, a golden batch trajectory may be calculated as an average or mean of the trajectories for all of the first-scale vessels. A trajectory similarity measure may be used to compare a predicted first trajectory for one of the first-scale vessels to the golden batch trajectory. For example, if the predicted first trajectory is more than a specified distance from the golden batch trajectory, then values determined from that first-scale vessel may be selectively excluded. Alternatively, if the predicted first trajectory is more than a specified distance from a trajectory of a nearest neighbor among the first-scale vessels, then values from the one of the first-scale vessels may be selectively excluded. The distance between two trajectories may be determined in various ways, e.g., a Euclidian distance, dynamic time warping (i.e., a dynamic programming approach to time series analysis) or longest common subsequence (to account for noise and outliers). Other approaches are also possible.

In addition, selective exclusion of process parameter values may be carried out by calculating multivariate scores. For example, a multivariate score for one of the first-scale vessels may be outside an accepted range or more than a specified distance from the golden batch trajectory. The multivariate score for the first-scale vessel may be derived from process parameter values and/or process output values determined from the fluid in the first-scale vessel. The multivariate score may be determined via the process parameters identified in the plan of step S101. Determination of the multivariate score may involve use of the batch evolution model, as well as multivariate statistical process control techniques, such as PCA, PLS, DMODX, or Hotelling's $T^2$ distribution.

Step S115 includes defining groups of the process parameter values according to a common characteristic. Each of the groups includes process parameter values determined from multiple ones of the first-scale vessels. The groups may be defined as discussed in more detail in connection with FIG. 6. The groups of process parameter values may consist of the remaining process parameter values. In other words, process parameter values that were selectively excluded in step S113 might not be included in any of the groups of the process parameter values.

Step S115 further comprises determining at least one statistically representative value for each of the groups of process parameter values. For example, the groups of process parameter values may be determined according to a moving average, and statistically representative values may be determined from an average of the process parameter values within each group (i.e., each group may have a corresponding statistically representative value). Defining the groups of the process parameter values may include determining multivariate scores from the process parameter values. In particular, multivariate statistical process control techniques may be used to determine components that describe the variance of multiple process parameters. The statistically representative values may then be determined from the components, e.g., as an average of the components.

The first trajectory may then be established from the statistically representative values.

Figure 2:
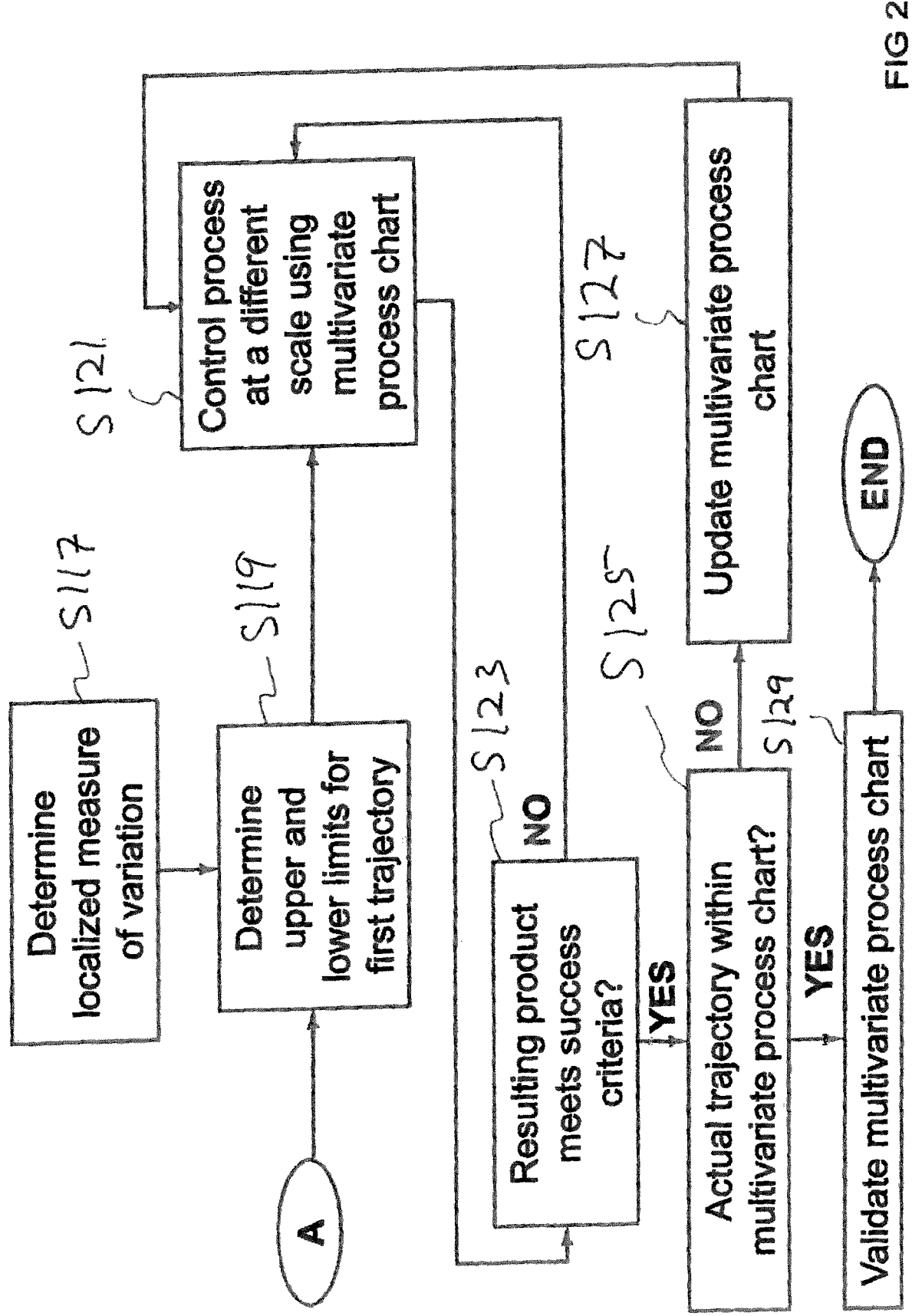
FIG. 2 shows further steps of the method for determining the multivariate process chart.

FIG. 2 shows steps S117 to S129 of the method for determining the multivariate process chart.

At step S117, acceptance criteria for the multivariate process chart may be determined. The acceptance criteria are be based on a measure of variation within each of the groups of process parameter values. Variation within a single group may be understood as a localized measure of variation.

For example, the acceptance criteria may be a function of the standard deviation within each of the groups. As an alternative to the standard deviation, the acceptance criteria may be based on a root mean square of a multivariate score and the golden batch trajectory of the first-scale vessels. The multivariate score may be derived from at least one process parameter value and/or at least one process output value.

Step S119 includes determining the upper limit and the lower limit of the multivariate process chart based on the measure of variation within each of the groups, e.g., according to the acceptance criteria.

The upper and lower limits may each be represented as separate lines, where the upper limit is above the first trajectory and the lower limit is below the first trajectory. The upper and lower limits may be based on a standard deviation from the first trajectory. In particular, a standard deviation may be calculated for each of the groups of process parameter values and the upper and lower limits may be derived from the standard deviation for each of the groups. In some cases, determining the upper limit and the lower limit comprises calculating a moving average of the standard deviation from the first trajectory and performing smoothing and interpolation to obtain separate lines (i.e., curves) above and below the first trajectory. Further, a multiple of the standard deviation may be used, e.g., between two and four times the standard deviation.

As an alternative to the standard deviation, the upper and lower limits may be based on the root mean square of a multivariate score and the golden batch trajectory of the first-scale vessels, as discussed in connection with step S117.

At step S121, the multivariate process chart, including the first trajectory and the upper and lower limits, may be used to control a process to produce a chemical, pharmaceutical, biopharmaceutical and/or biological product. The process may be carried out in a second-scale vessel. The second-scale vessel may contain fluid for producing the product and may have a size (i.e., volume) that differs by at least one order of magnitude from a size of one of the first-scale vessels. For example, a working volume of each of the first-scale vessels may be at least about 10-15 ml, or 250 ml, while a working volume of the second-scale vessel may be at least about 1 L, 2 L, 5 L, 10 L. 50 L, 200 L, 500 L, 1000 L, 2000 L. Process parameter values for multiple process parameters may be determined from the fluid in the second-scale vessel at the relatively high frequency. For example, for a nutrient level process parameter, a value may be determined from the fluid in the second-scale vessel at least once every three hours or at least once every two hours.

Accordingly, process parameter values may be determined from the fluid in the second-scale vessel online, as well as offline. Inline and atline determinations may also be made. Control of the process at the second-scale may occur late in process development, e.g., in a clinical trial or during manufacturing. A transfer function may be used to adapt process parameters (e.g., scale-dependent process parameters) used to control the process in the first-scale vessels for control of the process in the second-scale vessel.

An actual trajectory of the process may be calculated for comparison with the multivariate process chart. Completion of step S121 may result in production of the chemical, pharmaceutical, biopharmaceutical and/or biological product.

Step S123 may comprise determining whether the product meets at least one condition including or involving at least one process output and/or at least one process parameter. For example, the condition may involve evaluating a multivariate score determined from a plurality of process outputs against a specified value. The condition may be considered as success criteria or as part of the success criteria.

If the condition is not met, the multivariate process chart may be adapted respectively and step S121 may be carried out again. Further, the transfer function used at step S121 may be modified in order to increase the likelihood that the resulting product will meet the success criteria At step S125, the actual trajectory of the process calculated in step S121 may be compared with the multivariate process chart. If the actual trajectory is outside the upper limit or the lower limit of the multivariate process chart, then the upper limit or the lower limit may be updated at step S127, so that the actual trajectory is within the upper and lower limits.

If the actual trajectory is within the upper and lower limits (and the condition is met), then the multivariate process chart may be validated at step S129.

Figure 3:
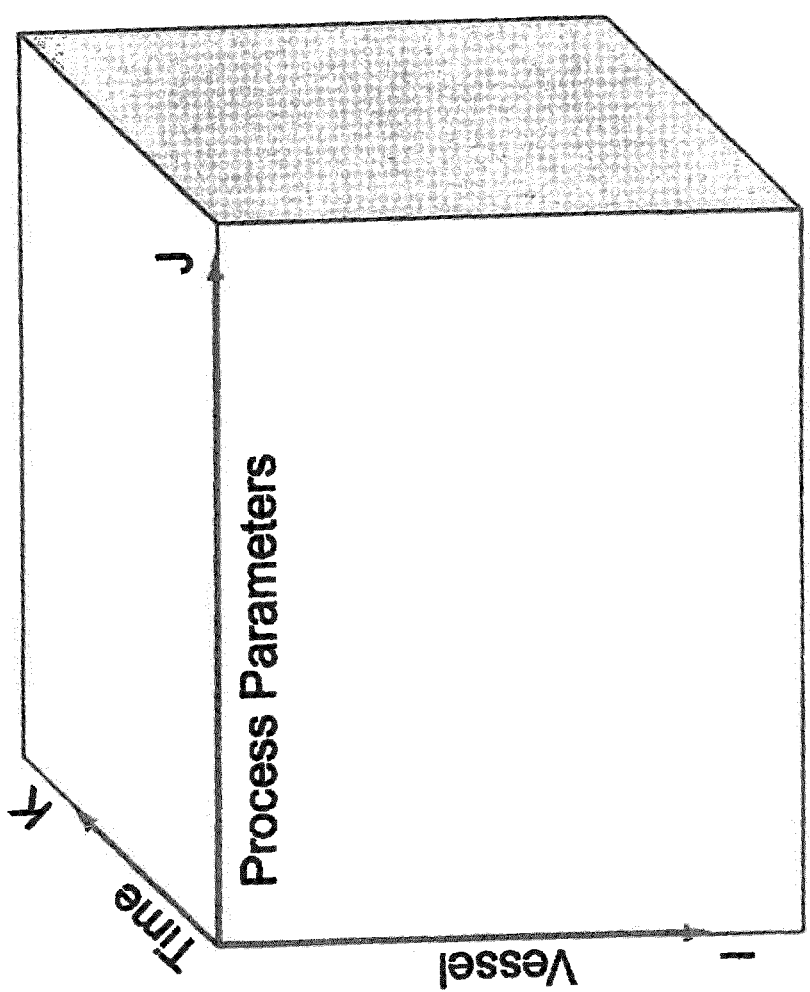
FIG. 3 shows the representation of data determined from the fluid in each of the first-scale vessels.

FIG. 3 shows a representation of process parameter values determined, at least in part by the first process control device, from the fluid in each of the first-scale vessels. The data may be represented in three dimensions, with the first dimension I for each of the vessels, the second dimension J for each of the process parameters and the third dimension K for the times when the values of the process parameters were measured. The representation is described in more detail in "Multi- and Megavariate Data Analysis—Basic Principles and Applications, Third revised edition L. Eriksson, T. Byrne, E. Johansson, J. Trygg and C. Vikström, page 288-289.

The process data may be stored in a computer in a three-dimensional array. Other data structures may also be used.

Figure 4:
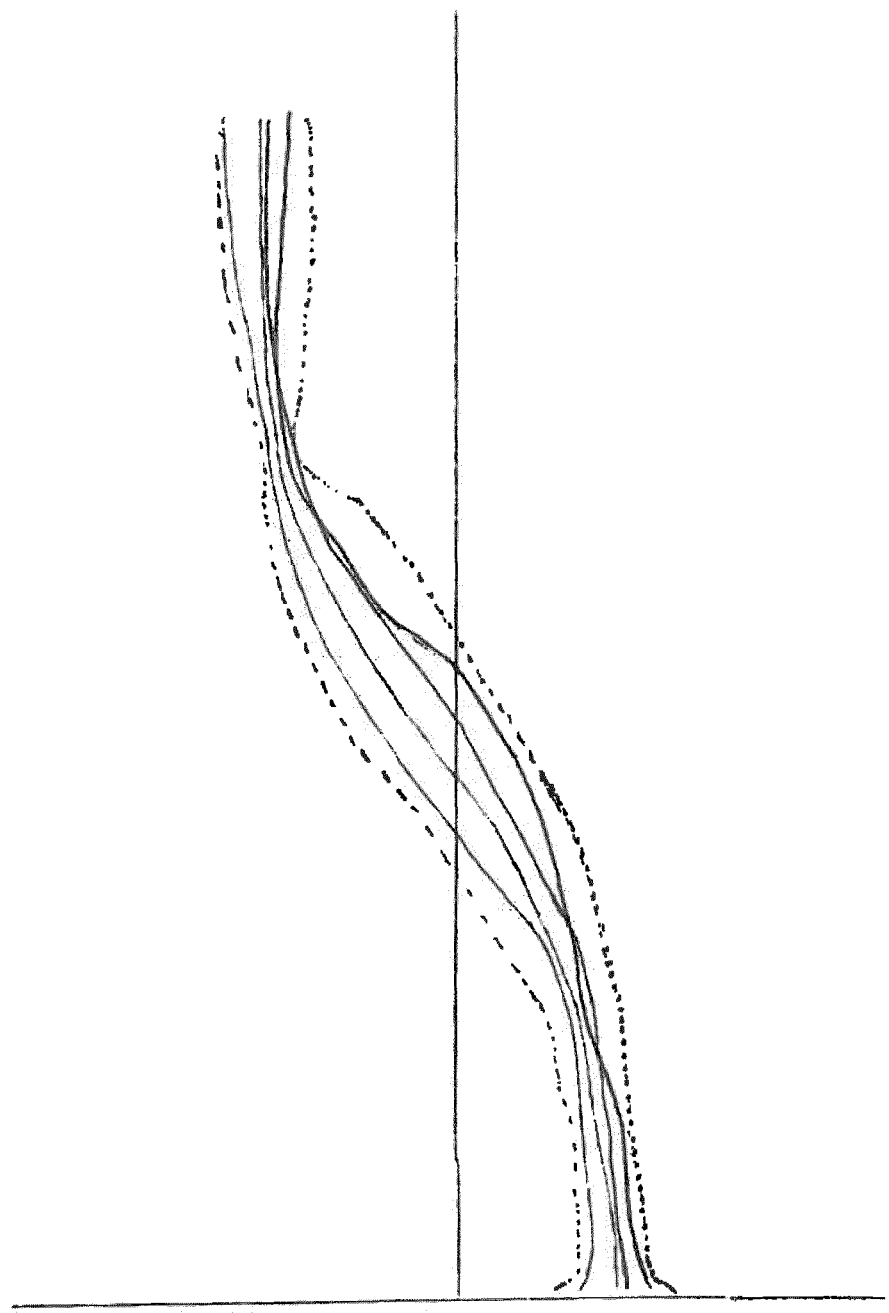
FIG. 4 shows a multivariate process chart determined according to conventional approaches.

FIG. 4 shows a multivariate process chart determined according to conventional approaches. In particular, the trajectories in the multivariate process chart may be formed from multivariate scores derived from process parameter values and/or process outputs. Because the multivariate process chart is derived using data determined at the relatively high frequency, in addition to data determined at the relatively low frequency, many values are available and smooth trajectory curves can be easily drawn.

A smooth trajectory curve may make it easier to control the process in the second-scale vessel. In particular, the smooth trajectory curve may make it easier to determine process deviations and ensure that a product meeting the success criteria is produced.

Figure 5:
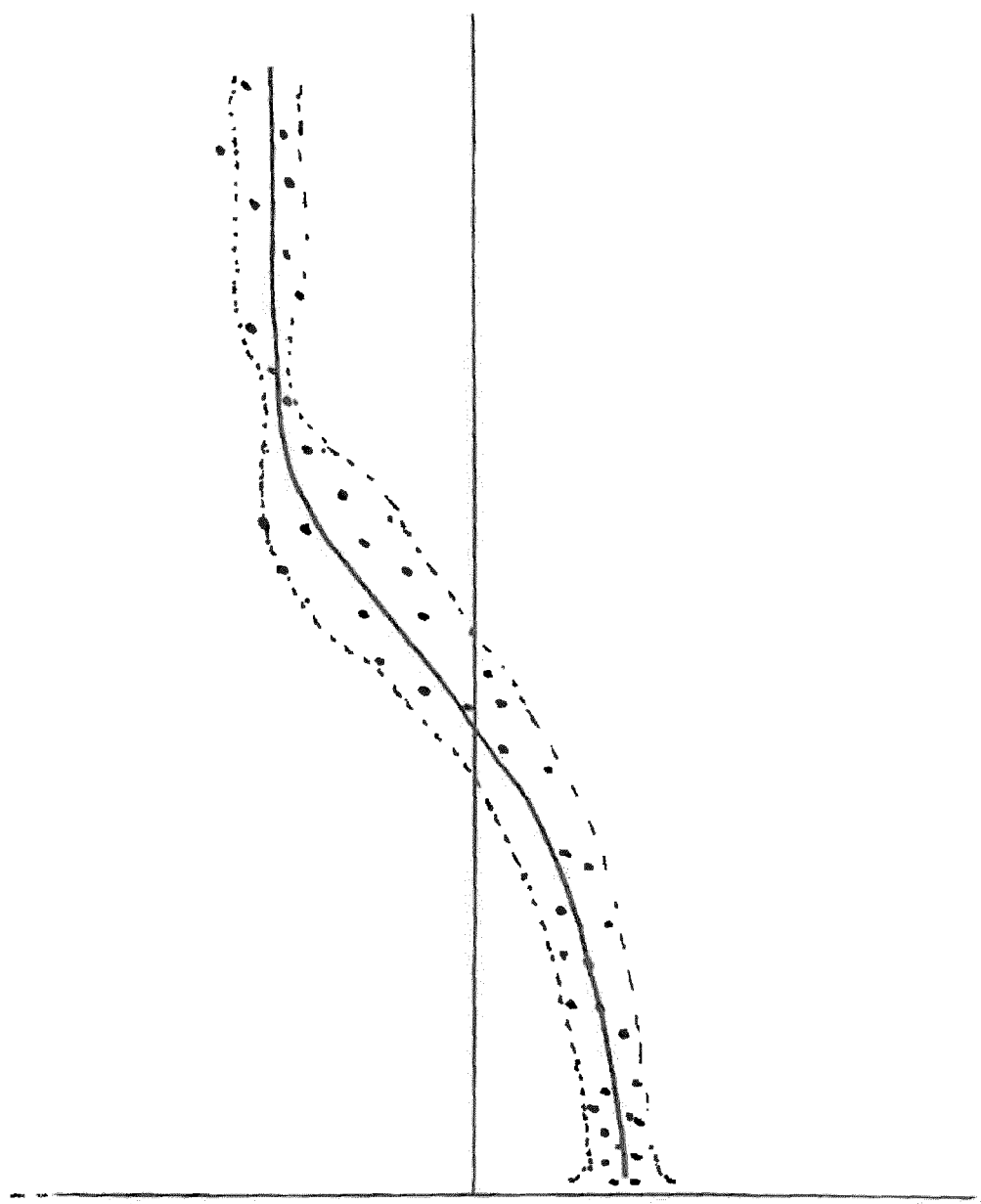
FIG. 5 shows a multivariate process chart determined according to techniques disclosed in the present application.

FIG. 5 shows a multivariate process chart determined according to techniques disclosed in the present application. In this case, the points shown are multivariate scores derived from process parameter values. There are not enough process parameter values shown in order to easily draw the smooth curves as provided in FIG. 4.

Accordingly, the multivariate process chart can be determined by defining groups according to a common characteristic and determining statistically representative values for each group, as described above. This technique results in a multivariate process chart that can be used on the second-scale, even though less process data is available. Thus, the multivariate process chart can be produced more quickly and is still effective for controlling the process at the second-scale.

Figure 6:
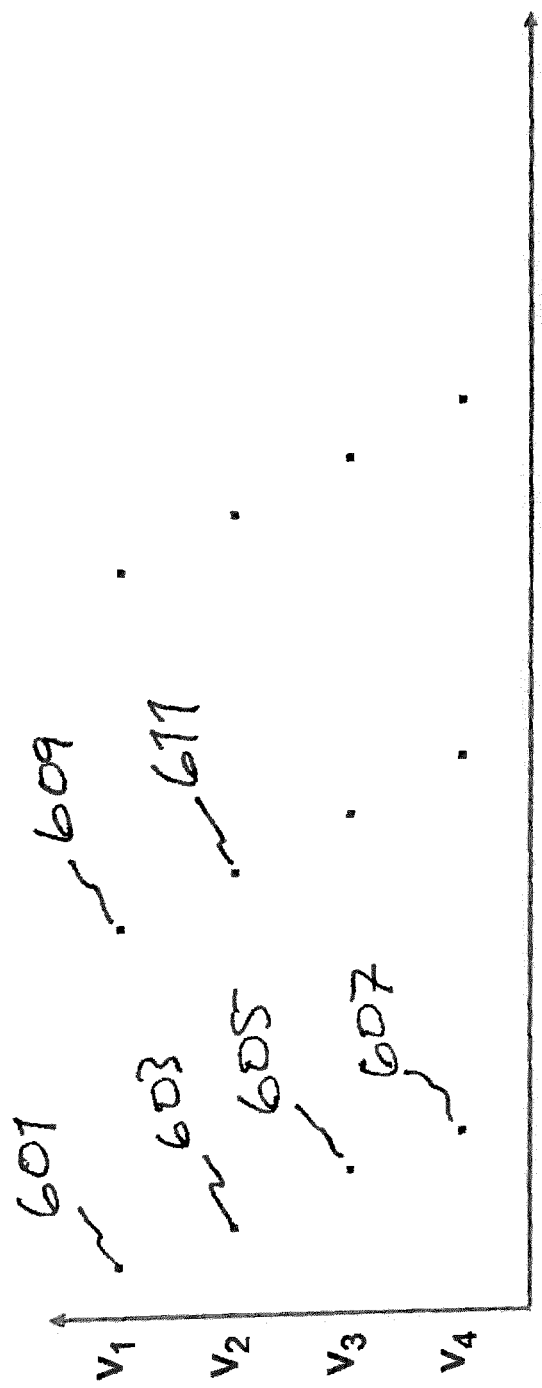
FIG. 6 shows process parameter values determined from four of the first-scale vessels over time.

FIG. 6 shows a simplified example of how groups of the process parameter values may be defined. In this case, the process parameter values are grouped according to sampling time as the common characteristic. Accordingly, process parameter values determined at similar times are gathered in the same group. A different statistically representative value may be determined for each of the groups.

Groups may be defined using a technique to smooth out short-term fluctuations in the process data, e.g., a moving average.

As depicted, vessels $v_1$, $v_2$, $v_3$ and $v_4$ are shown along the Y-axis. The X-axis shows the time at which the values were determined.

Accordingly, a first group may include parameter value 601 from vessel parameter value 603 from vessel $v_2$, parameter value 605 from vessel $v_3$, and parameter value 607 from vessel $v_4$. A statistically representative value for the first group may be the average of the values 601 to 607. A second group of process parameter values may include values 603, 605, 607, and 608. A statistically representative value for the second group may be the average of the values 603 to 608. Similarly, a third group of process parameter values may include parameter value 605, 607, 609, and 611. A statistically representative value for the third group may be the average of the values 605 to 611. Accordingly, each of the groups may include at least one value from each one of the vessels.

Further, values within the groups may overlap, such that one of the groups includes process parameter values that are also in another one of the groups. The present example shows a situation in which the common characteristic is a time interval during which the corresponding group of process parameter values was determined. In particular, the time interval may be a maximum duration between sample times. The maximum duration between sample times within a group of process parameter values may be the time required to sample all the vessels. For example, if there are 24 first-scale vessels and sampling all 24 vessels takes 6 hours, then 6 hours may be set as the maximum duration between sample times for any group of process parameter values.

However, process parameter values may also be grouped in other ways, for example, according to a process output value determined from the process parameter values or according to multivariate scores determined from the process parameter values (e.g., values 601-611 may be multivariate scores rather than process parameter values). In these cases, a moving average may also be used. Moreover, weights may be used in order to reduce the impact of outliers or to increase the impact of more recently obtained process data.

Figure 7:
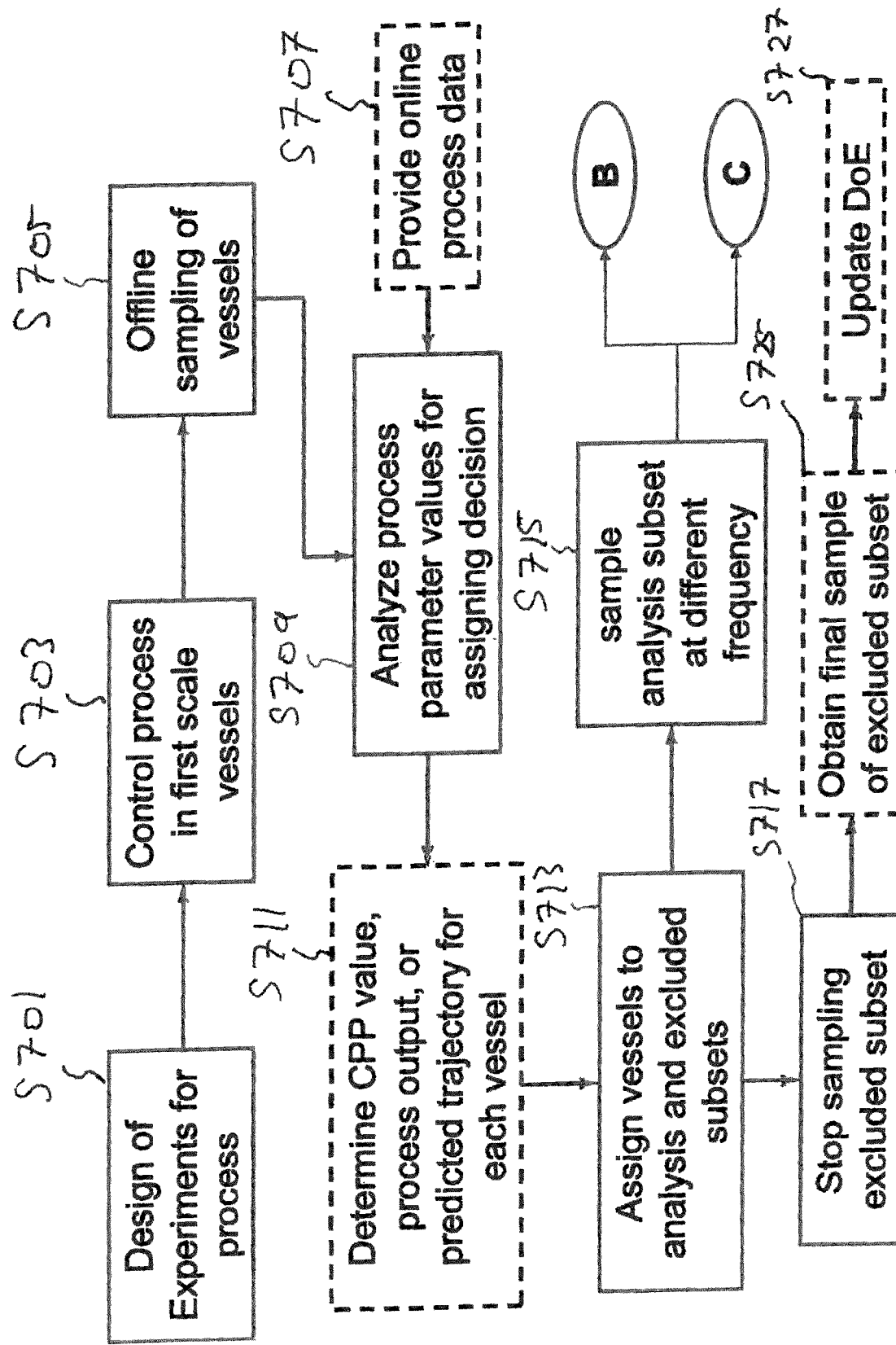
FIG. 7 shows steps of methods relating to a process carried out in a plurality of first-scale vessels via a first process control device.

FIG. 7 shows steps of a method for controlling a process in a plurality of first-scale vessels via the first process control device. In addition, FIG. 7 shows steps of a method for determining a multivariate process chart to be used to control a process to produce a chemical, pharmaceutical, biopharmaceutical and/or biological product.

Accordingly, steps S701 to S715, S717, S725 and S727 may be carried out by both methods. Further steps of the method for controlling a process in a plurality of first-scale vessels via a first process control device are indicated by the letter B. Further steps of the method for determining a multivariate process chart to be used to control a process to produce a chemical, pharmaceutical, biopharmaceutical and/or biological product are indicated by the letter C. Steps following the letters B and C are continued in FIG. 8.

Step S701 comprises receiving, by the first process control device, process parameters, the process parameters including process parameters to be controlled and process parameters to be measured.

Further, different conditions may be set for each of the first-scale vessels. In particular, process parameters to be controlled may be given different settings for each of the first-scale vessels. For example, a subset of the process parameters to be controlled (e.g., less than ½ or less than ⅓) may be set differently for each of the first-scale vessels. The process parameters to be controlled for the first-scale vessels may be specified according to a design of experiments.

Step S703 includes controlling, by the first process control device and at least partly in parallel, the process in each of the first-scale vessels.

While controlling the process, step S705 may be performed. Step S705 includes periodically determining, prior to an assigning decision and at a first frequency, first sets of process parameter values for each of the process parameters from each of the first-scale vessels. The determining may be carried out at a relatively low frequency. The determining may comprise sampling carried out offline or atline. The sampling may be carried out using a scientific instrument. For example, the samples may be analyzed using a spectrometer or a chemistry analyzer.

According to an example, the first process control device includes 24 first-scale vessels and the process is a fed-batch process. The process includes a three day initial phase (e.g., a batch phase). After three days, a transition occurs between the initial phase and a second phase (e.g., a continuous feeding phase).

Values for a nutrient level (i.e., nutrient concentration) process parameter are periodically determined by the scientific instrument using Raman spectroscopy. Determining a nutrient level value for one of the first-scale vessels takes 15 minutes. Thus, determining nutrient level values for all 24 of the first-scale vessels requires six hours. For efficient nutrient (e.g., glucose) control, more values are required. In particular, it would be desirable to obtain nutrient process parameter values from the vessels every three hours, even more preferably, every two hours.

Accordingly, the assigning decision is made after three days, i.e., at the transition between phases of the process. The assigning decision may be based on the process parameter values determined during the first three days of the process. In particular, the assigning decision may be based on the nutrient values obtained via Raman spectroscopy. Online data obtained from the first-scale vessels, e.g., temperature, pH, dissolved oxygen level, may also be used as a basis for the assigning decision.

The assigning decision may be based on predicted (i.e., estimated) trajectories determined for each of the first-scale vessels using the determined process parameter values. More particularly, the predicted trajectories of the first-scale vessels may be averaged to determine a golden batch trajectory. The first-scale vessels having predicted trajectories closest to the golden batch trajectory may be selected for the analysis subset and other first-scale vessels may be placed in the excluded subset. For example, about one third of the vessels may be placed in the analysis subset and about two thirds of the vessels may be placed in the excluded subset.

In some cases, the vessels in the excluded subset will not be sampled until a final sample is taken at the end of the process. The vessels in the analysis subset may be sampled at a second frequency (e.g., greater than the first frequency), which is possible because fewer vessels are being sampled by the first process control device. Therefore, it may be possible to obtain at least one Raman spectrum and nutrient level information every two hours. By obtaining a nutrient level value every two hours, nutrients may be effectively controlled in the vessels of the analysis subset.

Further, because of the greater frequency of sampling that is possible for vessels in the analysis subset, a nutrient control strategy (e.g., to maximize VCD and minimize use of nutrients) may be optimized. At the end of the process, all the vessels may be sampled and further analysis (e.g., spectroscopy measurements) may be performed. The final sampling of vessels in the excluded subset may be used to determine whether the assigning decision was correct. In particular, the correctness of the assigning decision may be assessed by determining whether the vessels in the analysis subset are higher performing; for example one or more process outputs for the fluid come closer to one or more success criteria (in comparison to fluid in the vessels of the excluded subset), or multivariate scores derived from process parameter values and/or process output values come closer to the success criteria.

At step S707, process parameter values determined online or atline may be provided for analysis prior to carrying out the assigning decision. These values may be determined directly by the first process control device. In particular, the scientific instrument might not be required.

At step S709, process parameter values may be analyzed for the assigning decision. In particular, univariate or multivariate statistical process control techniques may be used to analyze the process parameter values in order to facilitate the assigning decision.

At step S711, criteria for the assigning decision may be determined. In particular, at least one of the received process parameters may be identified as a critical process parameter. Values of the critical process parameter determined from the first-scale vessels may be compared to a first specified value (e.g., a target parameter value, such as a target nutrient level) in order to determine which of the first-scale vessels to place in the analysis subset and which to place in the excluded subset.

In addition or alternatively, process output values determined during step S705 may be compared to a second specified value (e.g., a target output value, such as a target VCD). Accordingly, vessels may be placed in the analysis subset or the excluded subset depending on how the process output values determined from the first-scale vessels compare to the second specified value.

A further criteria may be a predicted trajectory determined from the first-scale vessels. In particular, predicted trajectories may be determined for each of the first-scale vessels and compared to a specified trajectory. Accordingly, the assigning decision may be carried out based upon the comparison. The specified trajectory may be a golden batch trajectory determined as an average of the trajectories from the first-scale vessels.

A further criteria may be multivariate scores determined from process parameter values of each of the first-scale vessels. For example, a multivariate statistical process control technique may be used to determine components (i.e., principal components) representing multiple process parameters and describing variation of the process parameters. The multivariate scores may be used to determine a distance from a batch level model or a distance from a nearest neighbor (i.e., a multivariate score of a nearest neighbor), depending on the structure of the process parameter values. In particular, a distance from the batch level model may be used if process parameter values are clustered close together with fewer outliers, whereas a distance to the nearest neighbor may be used if there are more outliers or if the process parameter values are more spread out. Further multivariate statistical process control techniques, such as DMODX or Hoteling's $T^2$ distribution, may also be used.

The accepted range may vary depending on the process parameter or process output. For example, an accepted range for cell viability may be at least 90%. An accepted range for viable cell density may be at least five million cells per ml of fluid. An acceptable range for product titer may be at least 0.5 grams/L of fluid.

At step S713, the assigning decision may be carried out by assigning corresponding ones of the first-scale vessels to an analysis subset and other ones of the first-scale vessels to an excluded subset.

Step S715 comprises periodically determining, after the assigning decision and at the second frequency, second sets of process parameter values for each of the process parameters from the analysis subset of the first-scale vessels.

The first frequency is different from the second frequency. In particular, the second frequency may be greater than the first frequency. For example, resources (e.g., sampling resources) of the first process control device may focus entirely on the analysis subset of the first-scale vessels and stop sampling the excluded subset of the first-scale vessels. Accordingly, the process control device may cease determining process parameter values from the first-scale vessels of the excluded subset at step S717.

Even if the second frequency is not greater than the first frequency, a technical effect can still be realized. In particular, since process parameter values are no longer determined for vessels in the excluded subset after the assigning decision, resources (e.g., material such as nutrients or time required for a user to perform analysis) will be saved. These resources may be more productively used for other processes.

Figure 8:
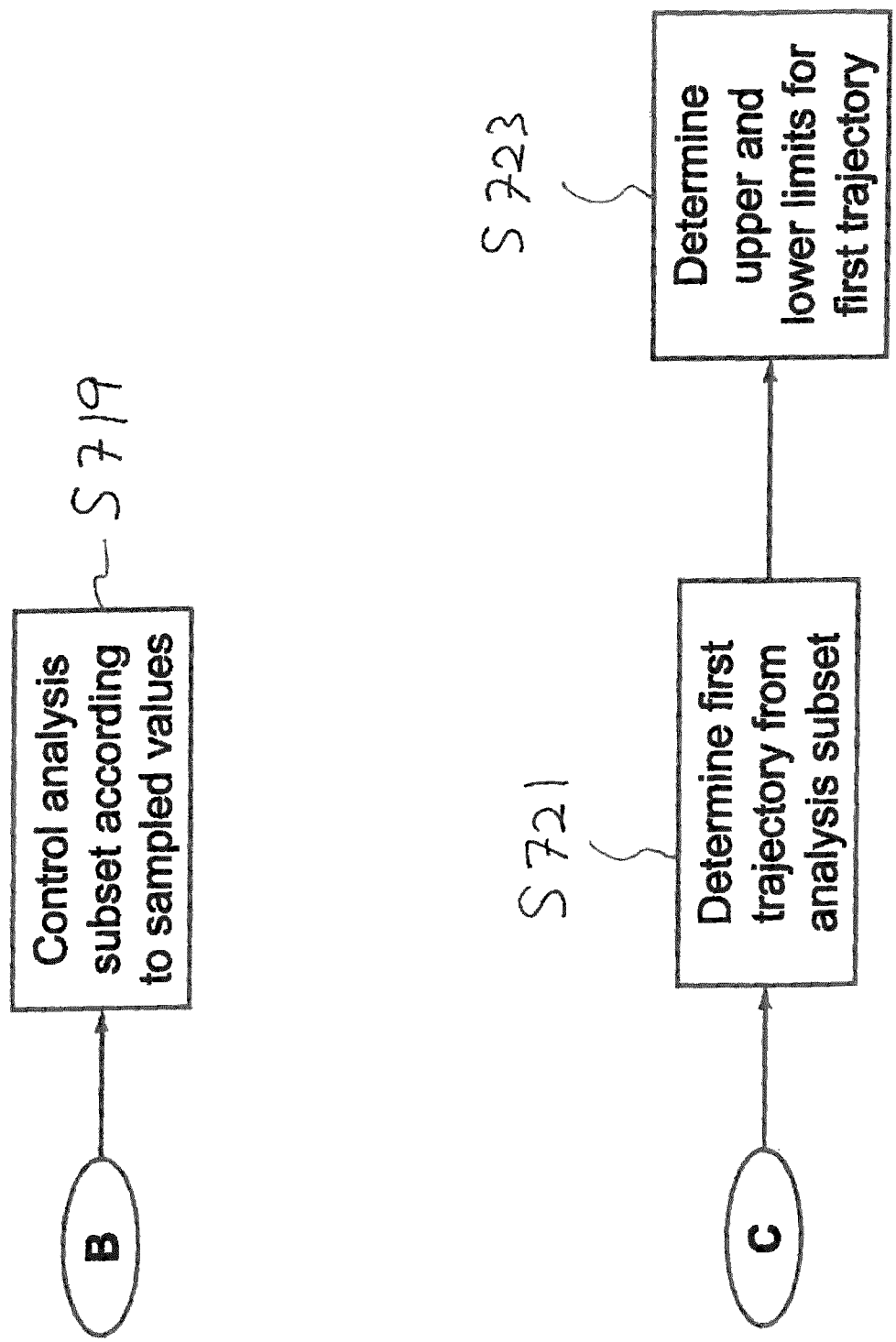
FIG. 8 shows further steps of the methods relating to the process carried out in the plurality of first-scale vessels via the first process control device.

FIG. 8 shows further steps of the method for controlling a plurality of first-scale vessels via the first process control device and the method for determining the multivariate process chart.

Step S719 relates to the method for controlling a plurality of first-scale vessels via the first process control device. Steps S721 and S723 relate to the method for determining the multivariate process chart.

Step S719 includes controlling, by the first process control device and at least partly in parallel, the process in the first-scale vessels of the analysis subset according to the second sets of process parameter values.

Returning to the method for determining the multivariate process chart, a first trajectory is established, at step S721, from the statistically representative values determined from process parameter values of each of the first-scale vessels in the analysis subset. The statistically representative values may be multivariate scores determined from the process parameter values. The statistically representative values may be averages of the multivariate scores or averages of the process parameter values themselves. The multivariate scores may be determined using multivariate statistical process control techniques such as PCA or PLS.

At step S723, upper and lower limits of the first trajectory are determined. The upper and lower limits are based on a measure of variation of the process parameter values for the first-scale vessels in the analysis subset. The upper and lower limits may be determined using various acceptance criteria. For example, the upper and lower limits may be based on a standard deviation of the process parameter values with respect to the first trajectory. Alternatively, the upper and lower limits may be based on a root mean square of a multivariate score of process parameter values and a corresponding point the first trajectory.

Returning to FIG. 7, at Step S725, final sets of process parameter values may be determined from the first-scale vessels in the excluded subset. The final sets of process parameter values from the vessels in the excluded subset may be compared to final sets of process parameter values determined from the first-scale vessels in the analysis subset. The comparison may enable a determination as to whether the assigning decision was correct. In particular, it may be possible to determine whether the vessels in the analysis subset achieved better results (met more success criteria) than the vessels in the excluded subset.

At step S727, the design of experiments used in step S701 may be updated according to the results. In particular, generalized subset designs may be used. Further details regarding generalized subset designs are provided in U.S. Pat. No. 9,746,850, dated Aug. 29, 2017.

Figure 9:
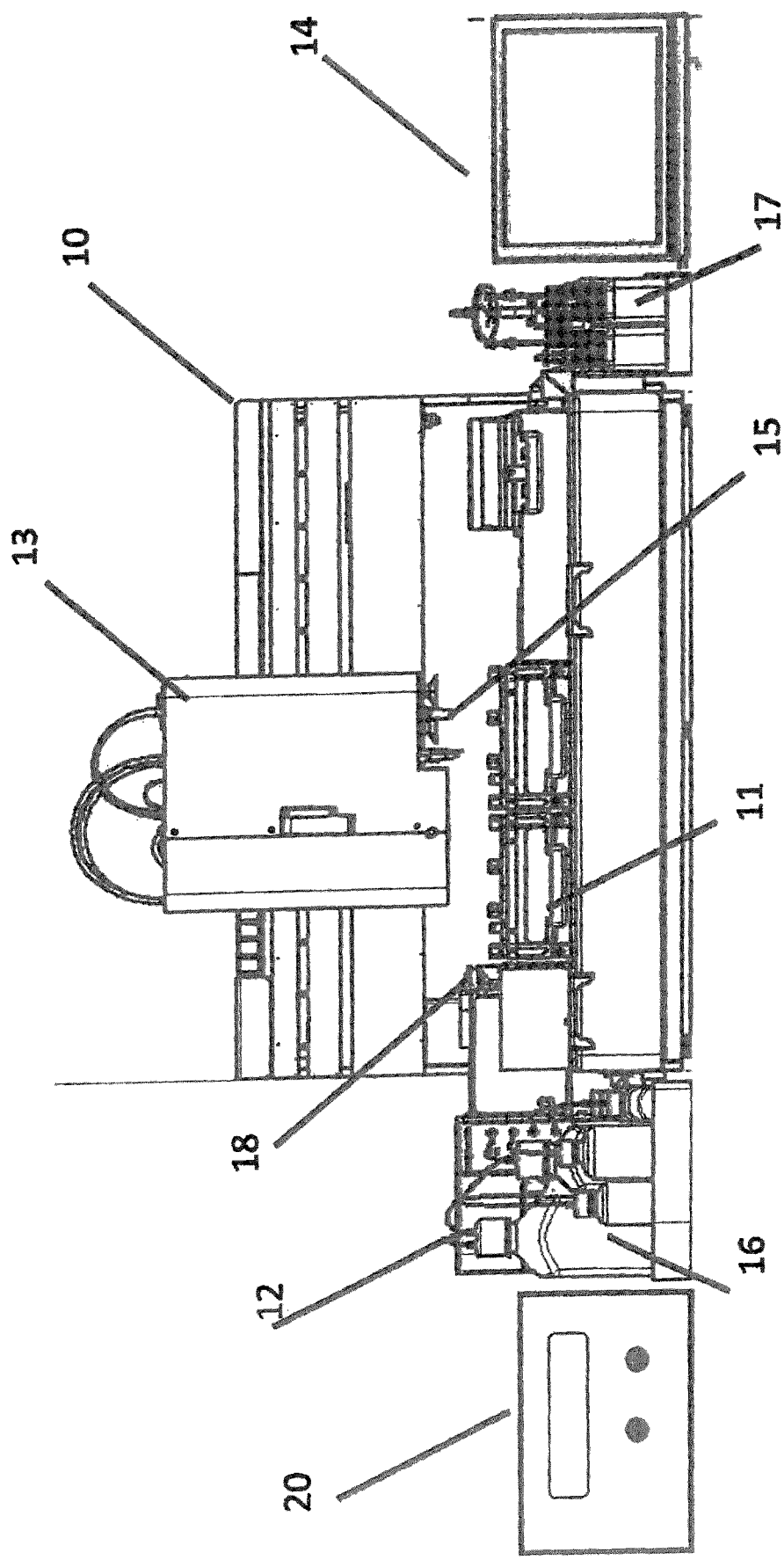
FIG. 9 shows a view of the first process control device.

A process control device 10 (possibly implemented as a bioreactor system) including an array of vessels (e.g., first-scale or micro-scale bioreactors) is shown in FIG. 9. The vessels are configured to contain fluid for producing a biopharmaceutical product (other types of fluid are also possible). The process control device 10 may correspond to the first process control device discussed above. The vessels may be located in a vessel station 11 (also referred to as a receiving station). The vessel station 11 is configured to receive a specified number of vessels, e.g., 6, 12 or 24. The process control device 10 is operable to control and/or monitor the vessels in the vessel station 11 at least partly in parallel, possibly entirely in parallel. The process control device 10 is operable to determine or set process parameters to be controlled (i.e., process control parameters). Examples of process parameters to be controlled include stirring speed and rate of gas supply.

The process control device 10 is operable to cause process parameter values to be periodically determined for process parameters (e.g., process parameters to be measured). The process parameter values may be determined directly from the vessels (e.g., via sensor spots) or from samples taken from the vessels. More particularly, the analysis module 12 may be used to process fluid (e.g., samples) from the vessels in order to determine process parameter values. Accordingly, the analysis module 12 may route fluid from the vessels to a scientific instrument (e.g., analysis instrument) to determine values for process parameters such as pH, cell count, metabolite level, nutrient level. pH values determine via the analysis module may be used for sensor calibration. The analysis module 12 may also support preparation of samples as well as cleaning and flushing after collecting samples.

The process control device 10 includes a robot, possibly implemented as a liquid handler 13. The robot is capable of addressing each first scale vessel, as well as dispensing and extracting fluid from the vessels. The liquid handler 13 performs automated process control and sampling. The liquid hander 13 collects (or draws) samples from each individual vessel in the vessel station 11 and feeds nutrients or detergent (e.g. acid, base, antifoam, etc.) to each individual vessel. These tasks may also be performed by the robot in implementations than the liquid handler 13.

The process control device 10 may include a process control module 14 (also referred to as a workstation). The process control module 14 includes a user interface (e.g., input device(s) such as a keyboard, output device(s) such as a display, processing means, storage). The process control module may store a process control strategy to control the process control device 10, more specifically, to control the liquid handler 13 and the analysis module 12. In particular, the process control device may store values for process parameters to be controlled (i.e., control set points). Further, the process control device may store a recipe for the process.

The process control device 10 may include a sampling device 15. More specifically, the liquid handler 13 may include the sampling device 15. The sampling device 15 may implement an automated pipetting system and/or carry pipet tips.

The process control device 10 may include liquids 16 to supply to the analysis module 12. The liquids 16 may include cleaning and rinsing agents, pH buffers, calibration solutions, etc.

The analysis module 12 and the process control module 14 may be combined in a controller.

Storage containers 17 may be used to store liquids to be supplied to the vessels. The liquids from the storage containers 17 may be supplied by the process control device 10, particularly the liquid handler 13. The liquids may include glucose feed, acids, bases, antifoam solution, etc.

The process control device 10 may include a sample holder or receptacle, possibly implemented as sample cup 18. More particularly, the sample cup 18 may be part of the analysis module 12. The sample cup 18 may be configured to receive a sample taken by the liquid handler 13 and/or the sampling device 15, and to feed the sample to the analysis module 12 as well as to further analytical devices.

The process control device 10 may include a scientific instrument, possibly in the form of analytical device 20. The analytical device 20 may be implemented as a Raman measurement system (i.e., spectrometer), a high performance liquid chromatography (HPLC) device, or a mass spectrometry device. There may be multiple analytical devices (not shown). The analytical device 20 may be configured to receive samples from the analysis module 12 and perform analytical measurements to determine process parameter values such as glucose, glutamine, lactate or process outputs such as VCD, titer. The process outputs may also include product quality attributes, such as glycosylation.

One or more heaters or chillers (not shown) may be located adjacent to the vessel station 11 to control the temperature of the vessels.

Figure 10:
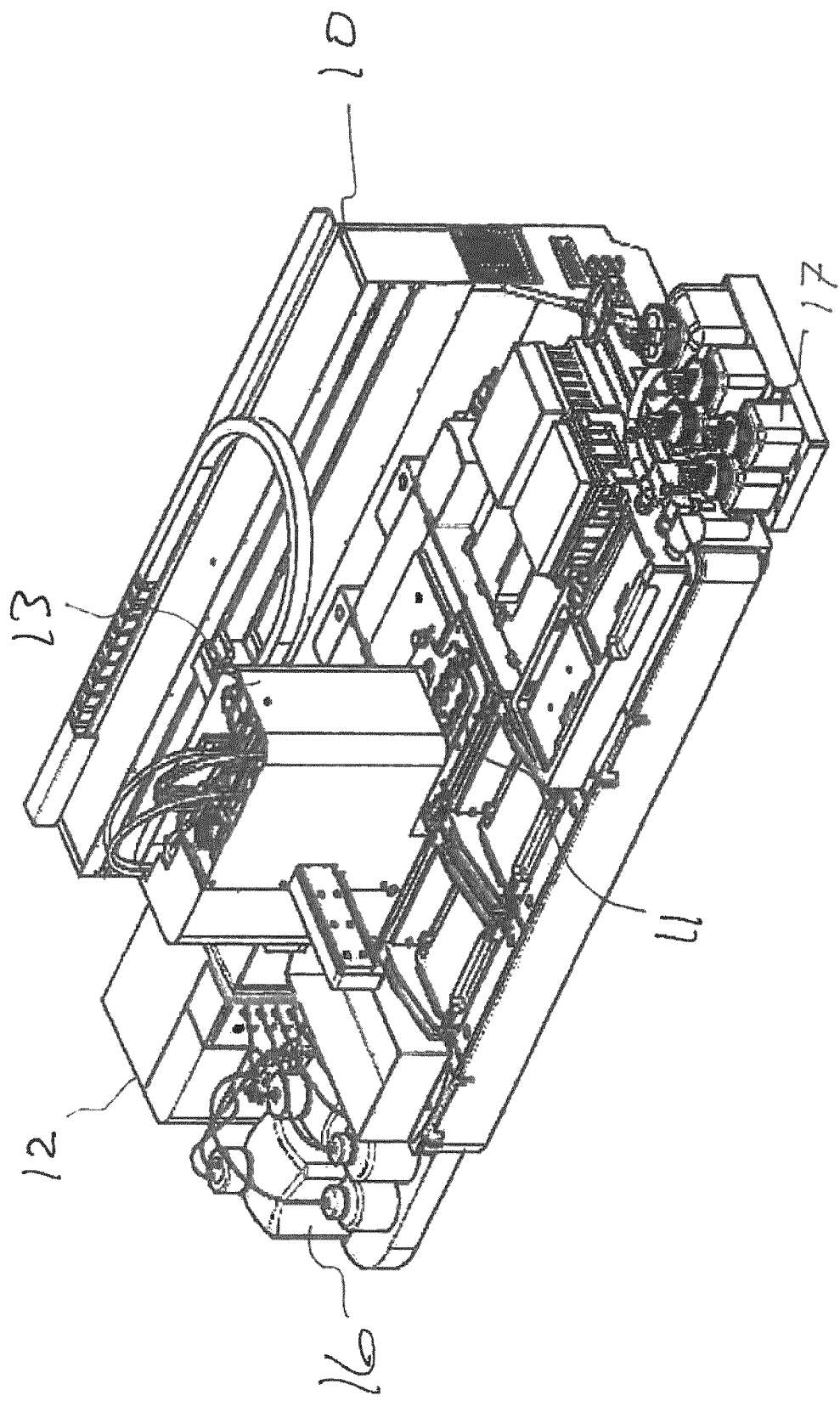
FIG. 10 shows another view of the first process control device.

FIG. 10 shows the process control device of FIG. 9 from an overhead perspective.

The invention claimed is:

1. A computer-implemented method for controlling a process in a plurality of first scale vessels via a first process control device, wherein each of the first scale vessels contains fluid, wherein the process is for producing a chemical, pharmaceutical, biopharmaceutical and/or biological product, the method comprising:

receiving, by the first process control device, process parameters, the process parameters including process parameters to be controlled and process parameters to be measured;

controlling, by the first process control device and at least partly in parallel, the process in each of the first scale vessels;

periodically determining, prior to an assigning decision and at a first frequency, first sets of process parameter values for each of the process parameters from each of the first scale vessels;

carrying out the assigning decision by assigning corresponding ones of the first scale vessels to an analysis subset and other ones of the first scale vessels to an excluded subset in order to focus resources of the first process control device on determining process parameter values from the first scale vessels in the analysis subset;

periodically determining, after the assigning decision and at a second frequency, second sets of process parameter values for each of the process parameters from the analysis subset of the first scale vessels, wherein the second frequency is greater than the first frequency;

cease determining, by the process control device, process parameter values from the first scale vessels of the excluded subset; and controlling, by the first process control device and at least partly in parallel, the process in the first scale vessels of the analysis subset according to the second sets of process parameter values.

2. The method of claim 1, wherein controlling the process in the first scale vessels of the analysis subset further comprises:

deriving a process output value from at least one of the first scale vessels in the analysis subset; and initiating a control action via the first process control device in order to optimize the process output value, wherein the control action includes increasing or decreasing a supply of a nutrient.

3. The method of claim 1, wherein the assigning decision is carried out at a transition between phases of the process, after a specified number of sets of process parameter values have been determined or at a specified time.

4. The method of claim 1, wherein the assigning decision is carried out according to at least one of the following criteria:

i. at least one of the process parameters is identified as a critical process parameter, and the first sets of values of the critical process parameter determined fom one of the corresponding ones of the first scale vessels are closer to a first specified value than the first sets of values determined the other ones of the first scale vessels, ii. process output values determined from one of the corresponding ones ofthe first scale vessels are closer to a second specified value than process output values determined from one of the other ones of the first scale vessels;

iii. a predicted trajectory for a corresponding one of the first scale vessels is closer to a specified trajectory than a predicted trajectory for one of the other ones of the first scale vessels;
iv. score values calculated by multivariate data analysis for one of the corresponding ones of the first scale vessels is within an accepted range of the specified trajectory, wherein the score values are derived from the first sets of process parameter values for the corresponding first scale vessel.

5. The method of claim 1, wherein the periodically determining comprises:
collecting, by the first process control device, samples from at least one of the first scale vessels; and
analyzing, by a scientific instrument, the samples, wherein the scientific instrument is a substance or molecule identification instrument,
wherein the scientific instrument is one of the following:
a spectrometer,
a mass spectrometer, or
a chromatography system including a chromatograph for separation of analytes and a detecting instrument for qualitative and quantitative detection of the analytes after their separation.

6. The method of claim 5, wherein the first sets of process parameter values and the second sets of process parameter values include data directly determined by the first process control device and data determined, at least in part, by the scientific instrument.

7. The method of claim 1, wherein the first frequency and the second frequency are each dependent on a capability of the first process control device.

8. The method of claim 7, wherein the second frequency is at least about 10% greater than the first frequency.

9. The method of claim 7, wherein the capability is a collecting and/or sampling speed;
wherein the capability depends on one or more of the following: the number of vessels, a speed of the first process control device, other requirements of the first process control device relating to control of the process and/or use of sampling resources.

10. The method of claim 7, wherein the second frequency is at least about 25% greater than the first frequency.

11. The method of claim 7, wherein the second frequency is at least about 50% greater than the first frequency.

12. The method of claim 7, wherein the second frequency is at least about 100% greater than the first frequency.

13. The method of claim 1, determining a final set of process parameter values from each of the first scale vessels in the excluded subset; and
according to the final set of process parameter values, updating a design of experiments and/or validating the assigning decision.

14. The method of claim 1, wherein periodically determining the second sets of process parameter values further comprises:
determining, for each of the first scale vessels in the analysis subset, a predicted trajectory from the process parameter values of a corresponding one of the first scale vessels; and
when the predicted trajectory deviates from a specified trajectory by more than a tolerance value, reassigning the corresponding first scale vessel from the analysis subset of the first scale vessels to the excluded subset of the first scale vessels.

15. The method of claim 1, wherein the each of the first scale vessels has at least one of the following characteristics:
it is a bioreactor or a microbioreactor;
it includes stirring means for stirring its contents;
it includes a gas delivery means;
it includes at least one sensor for measuring at least one of the following: pH, dissolved oxygen, or temperature;
it has a volume of 1 ml up to 2000 L; and
it is disposable.

16. A computer program comprising computer-readable instructions, which, when loaded and executed on a computer system, cause the computer system to perform operations according to the method of claim 1.

17. A computer-implemented method for determining a multivariate processchart, the multivariate process chart to be used to control a process to produce a chemical, pharmaceutical, biopharmaceutical and/or biological product, the multivariate process chart including a first trajectory, an upper limit for the first trajectory and a lower limit for the first trajectory, the method comprising:
providing a plurality of first scale vessels, each of the first scale vessels containing fluid for producing the product;
receiving, by a first process control device, process parameters, the process parameters including process parameters to be controlled and process parameters to be measured;
controlling, by the first process control device and at least partly in parallel, the process in each of the first scale vessels;
periodically determining, prior to an assigning decision and at a first frequency, first sets of process parameter values for each of the process parameters from each of the first scale vessels;
carrying out the assigning decision by assigning corresponding ones of the first scale vessels to an analysis subset and other ones of the first scale vessels to an excluded subset in order to focus resources of the first process control device on determining process parameter values from the first scale vessels in the analysis subset;
periodically determining, after the assigning decision and at a second frequency, second sets of process parameter values for each of the process parameters from the analysis subset of the first scale vessels, wherein the second frequency is greater than the first frequency;
cease determining, by the process control device, process parameter values from the first scale vessels of the exclude subset;
determining statistically representative values from the process parameter values of each of the first scale vessels in the analysis subset;
establishing the first trajectory from the statistically representative values; and
determining the upper limit and the lower limit based on a measure of variation of the process parameter values for the first scale vessels in the analysis subset.

18. A computer-implemented method of controlling a process to produce a chemical, pharmaceutical, biopharmaceutical and/or biological product using the multivariate process chart of claim 3, the method comprising:
providing at least one second scale vessel, the second scale vessel containing fluid for producing the product, wherein a size of the second scale vessel differs by at least one order of magnitude from a size of one of the first scale vessels;

receiving, by a second process control device, the process parameters;

carrying out, by the second process control device, the following steps:

controlling the process in the second scale vessel;

periodically determining process parameter values for the process parameters from the fluid in the second scale vessel;

estimating an actual trajectory of the process from the process parameter values; and when a deviation of the actual trajectory from the first trajectory exceeds the upper limit or the lower limit, controlling the process to correct the deviation, thereby influencing at least one of the process parameters.

19. A process control device for determining the multivariate process chart of claim 17, the device comprising:

the plurality of first scale vessels;

a robot capable of addressing each first scale vessel, dispensing fluid to the first scale vessels, and extracting samples of fluid; and the first process control device.

20. A process control device for controlling a process to produce a chemical, pharmaceutical, biopharmaceutical and/or biological product, the device comprising:

a plurality of first scale vessels, each of the first scale vessels being configured to contain fluid for producing the product;

a robot capable of addressing each first scale vessel, dispensing fluid to the first scale vessels, and extracting samples of fluid;

a controller operable to:

receive process parameters, the process parameters including process parameters to be controlled and process parameters to be measured;

control, at least partly in parallel, the process in each of the first scale vessels;

periodically determine, prior to an assigning decision and at a first frequency, first sets of process parameter values for each of the process parameters from each of the first scale vessels;

carry out the assigning decision by assigning corresponding ones of the first scale vessels to an analysis subset and other ones of the first scale vessels to an excluded subset in order to focus resources of the first process control device on determining process parameter values from the first scale vessels in the analysis subset;

periodically determine, after the assigning decision and at a second frequency, second sets of process parameter values for each of the process parameters from the analysis subset of the first scale vessels, wherein the second frequency is greater than the first frequency;

cease determining, by the process control device, process parameter values from the first scale vessels of the exclude subset; and control, at least partly in parallel, the process in each of the first scale vessels according to the second sets of process parameter values.

\* \* \* \* \*

UNITED STATES PATENT AND TRADEMARK OFFICE
CERTIFICATE OF CORRECTION

PATENT NO. : 12,422,803 B2
APPLICATION NO. : 17/433586
DATED : September 23, 2025
INVENTOR(S) : Grimm et al.

Page 1 of 1

It is certified that error appears in the above-identified patent and that said Letters Patent is hereby corrected as shown below:

In the Claims

Column 34, Lines 59-62, Claim 4 "the corresponding ones of the first scale vessels are closer to a first specified value than the first sets of values determined the other ones of the first scale vessels," should read -- the corresponding ones of the first scale vessels are closer to a first specified value than the first sets of values determined from the other ones of the first scale vessels --

Column 34, Lines 63-64, Claim 4 "process output values determined from one of the corresponding ones ofthe first scale vessels are closer to" should read -- process output values determined from one of the corresponding ones of the first scale vessels are closer to --

Signed and Sealed this
Twenty-seventh Day of January, 2026

John A. Squires
*Director of the United States Patent and Trademark Office*